(12) United States Patent
Sanchez

(10) Patent No.: US 11,551,644 B1
(45) Date of Patent: Jan. 10, 2023

(54) ELECTRONIC INK DISPLAY FOR SMART RING

(71) Applicant: BlueOwl, LLC, San Francisco, CA (US)

(72) Inventor: Kenneth Jason Sanchez, San Francisco, CA (US)

(73) Assignee: BlueOwl, LLC, San Francisco, CA (US)

( * ) Notice: Subject to any disclaimer, the term of this patent is extended or adjusted under 35 U.S.C. 154(b) by 0 days.

(21) Appl. No.: 16/927,234

(22) Filed: Jul. 13, 2020

Related U.S. Application Data

(60) Provisional application No. 62/877,391, filed on Jul. 23, 2019, provisional application No. 62/981,089, filed on Feb. 25, 2020.

(51) Int. Cl.
*G09G 5/34* (2006.01)
*G06F 3/16* (2006.01)
(Continued)

(52) U.S. Cl.
CPC ............. *G09G 5/34* (2013.01); *A61B 5/0002* (2013.01); *A61B 5/18* (2013.01); *A61B 5/4809* (2013.01);
(Continued)

(58) Field of Classification Search
CPC .. G09G 5/34; G09G 2380/10; G09G 2354/00; G06F 3/041; G06F 3/167;
(Continued)

(56) References Cited

U.S. PATENT DOCUMENTS

| 6,097,480 A | 8/2000 | Kaplan |
| 6,560,993 B1 | 5/2003 | Bosque et al. |

(Continued)

FOREIGN PATENT DOCUMENTS

| CN | 104799509 A | 7/2015 |
| CN | 106360895 A | 2/2017 |

(Continued)

OTHER PUBLICATIONS

"How to find your ideal bedtime with the Oura app", available online at <https://web.archive.org/web/20191206205332/https://ouraring.com/how-to-find-your-ideal-bedtime-with-the-oura-app/>, 2019, 8 pages.

(Continued)

*Primary Examiner* — Grant Sitta
(74) *Attorney, Agent, or Firm* — Faegre Drinker Biddle & Reath LLP

(57) ABSTRACT

A system for displaying information indicative of driving conditions, to a driver, using a smart ring are disclosed. An exemplary system includes a smart ring with a ring band having a plurality of surfaces including an inner surface, an outer surface, a first side surface, and a second side surface. The system further includes a processor, configured to obtain data from a communication module within the ring band, or from one or more sensors disposed within the ring band. The obtained data are representative of information indicative of one or more driving conditions to be displayed to the driver. The smart ring also includes an electronic ink (e-ink) display disposed on at least one of the plurality of surfaces, and configured to present information indicative of the one or more driving conditions.

20 Claims, 7 Drawing Sheets

(51) Int. Cl.
*G06F 3/041* (2006.01)
*G08G 1/0967* (2006.01)
*A61B 5/18* (2006.01)
*A61B 5/00* (2006.01)

(52) U.S. Cl.
CPC ............ *A61B 5/4845* (2013.01); *A61B 5/681* (2013.01); *G06F 3/041* (2013.01); *G06F 3/167* (2013.01); *G08G 1/0967* (2013.01); *G09G 2354/00* (2013.01); *G09G 2380/10* (2013.01)

(58) Field of Classification Search
CPC ..... A61B 5/0002; A61B 5/681; A61B 5/4845; A61B 5/4809; A61B 5/18; G08G 1/0967
See application file for complete search history.

(56) References Cited

U.S. PATENT DOCUMENTS

| | | | |
|---|---|---|---|
| 7,013,674 | B2 | 3/2006 | Kretchmer |
| 7,500,746 | B1 | 3/2009 | Howell et al. |
| 7,872,444 | B2 | 1/2011 | Hamilton et al. |
| 8,446,275 | B2 | 5/2013 | Utter, II |
| 8,570,273 | B1 | 10/2013 | Smith |
| 9,362,775 | B1 | 6/2016 | Jacobs |
| 9,420,260 | B2 | 8/2016 | Mcgregor et al. |
| 9,477,146 | B2 | 10/2016 | Xu et al. |
| 9,509,170 | B2 | 11/2016 | Wu |
| 9,628,707 | B2 | 4/2017 | Blum et al. |
| 9,660,488 | B2 | 5/2017 | Breedvelt-Schouten et al. |
| 9,696,690 | B2 | 7/2017 | Nguyen et al. |
| 9,711,060 | B1 | 7/2017 | Lusted et al. |
| 9,711,993 | B2 | 7/2017 | Kim |
| 9,717,949 | B1 | 8/2017 | Tran et al. |
| 9,756,301 | B2 | 9/2017 | Li et al. |
| 9,847,020 | B2 | 12/2017 | Davis |
| 9,861,314 | B2 | 1/2018 | Haverinen et al. |
| 9,908,530 | B1 | 3/2018 | Fields et al. |
| 9,955,286 | B2 | 4/2018 | Segal |
| 9,956,963 | B2 | 5/2018 | Vijaya Kumar et al. |
| 9,965,761 | B2 | 5/2018 | Elangovan et al. |
| 10,007,355 | B2 | 6/2018 | Schorsch et al. |
| 10,085,695 | B2 | 10/2018 | Ouwerkerk et al. |
| 10,099,608 | B2 | 10/2018 | Cuddihy et al. |
| 10,102,510 | B2 | 10/2018 | Yau et al. |
| 10,137,777 | B2 | 11/2018 | Lu et al. |
| 10,317,940 | B2 | 6/2019 | Eim et al. |
| 10,359,846 | B2 | 7/2019 | Priyantha et al. |
| 10,366,220 | B2 | 7/2019 | Shapiro et al. |
| 10,396,584 | B2 | 8/2019 | Madau et al. |
| 10,409,327 | B2 | 9/2019 | Stotler |
| 10,444,834 | B2 | 10/2019 | Vescovi et al. |
| 10,463,141 | B2 | 11/2019 | Fitzgerald et al. |
| 10,629,175 | B2 | 4/2020 | Yan et al. |
| 10,664,842 | B1 | 5/2020 | Bermudez et al. |
| 10,693,872 | B1 | 6/2020 | Larson et al. |
| 10,703,204 | B2* | 7/2020 | Hassan ................ B60K 28/14 |
| 10,745,032 | B2 | 8/2020 | Scheggi |
| 11,227,060 | B1 | 1/2022 | John et al. |
| 2002/0121831 | A1 | 9/2002 | Egawa et al. |
| 2005/0230596 | A1 | 10/2005 | Howell et al. |
| 2008/0068559 | A1 | 3/2008 | Howell et al. |
| 2008/0218684 | A1 | 9/2008 | Howell et al. |
| 2011/0007035 | A1 | 1/2011 | Shai |
| 2012/0184367 | A1 | 7/2012 | Parrott et al. |
| 2014/0107493 | A1 | 4/2014 | Yuen et al. |
| 2014/0118704 | A1 | 5/2014 | Duelli et al. |
| 2014/0120983 | A1 | 5/2014 | Lam |
| 2014/0218529 | A1* | 8/2014 | Mahmoud .......... H04N 5/23241 348/148 |
| 2014/0238153 | A1 | 8/2014 | Wood et al. |
| 2015/0046996 | A1 | 2/2015 | Slaby et al. |
| 2015/0062086 | A1 | 3/2015 | Nattukallingal |
| 2015/0124096 | A1* | 5/2015 | Koravadi ............ G06V 20/584 348/148 |
| 2015/0126824 | A1 | 5/2015 | Leboeuf et al. |
| 2015/0158499 | A1* | 6/2015 | Koravadi ............ B62D 15/029 701/1 |
| 2015/0220109 | A1 | 8/2015 | Von et al. |
| 2015/0277559 | A1* | 10/2015 | Vescovi ................ G06F 1/163 345/173 |
| 2015/0338926 | A1* | 11/2015 | Park ...................... G06F 3/011 345/156 |
| 2015/0352953 | A1* | 12/2015 | Koravadi ............. B60K 37/06 701/36 |
| 2016/0028267 | A1 | 1/2016 | Lee et al. |
| 2016/0226313 | A1 | 8/2016 | Okubo |
| 2016/0236692 | A1 | 8/2016 | Kleen et al. |
| 2016/0292563 | A1* | 10/2016 | Park ................... G06F 3/04883 |
| 2016/0317060 | A1 | 11/2016 | Connor |
| 2016/0334901 | A1 | 11/2016 | Rihn |
| 2017/0010677 | A1* | 1/2017 | Roh ..................... G06F 1/163 |
| 2017/0012925 | A1 | 1/2017 | Tekin et al. |
| 2017/0024008 | A1 | 1/2017 | Kienzle et al. |
| 2017/0026790 | A1 | 1/2017 | Flitsch et al. |
| 2017/0042477 | A1 | 2/2017 | Haverinen et al. |
| 2017/0053461 | A1* | 2/2017 | Pal ....................... H04W 4/027 |
| 2017/0070078 | A1 | 3/2017 | Hwang et al. |
| 2017/0075701 | A1* | 3/2017 | Ricci ............... H04N 21/43637 |
| 2017/0080952 | A1 | 3/2017 | Gupta et al. |
| 2017/0090475 | A1 | 3/2017 | Choi et al. |
| 2017/0109512 | A1 | 4/2017 | Bower et al. |
| 2017/0129335 | A1 | 5/2017 | Lu et al. |
| 2017/0131772 | A1 | 5/2017 | Choi |
| 2017/0190121 | A1 | 7/2017 | Aggarwal et al. |
| 2017/0242428 | A1* | 8/2017 | Pal ....................... B60K 37/06 |
| 2017/0346635 | A1 | 11/2017 | Gummeson et al. |
| 2017/0347895 | A1 | 12/2017 | Wei et al. |
| 2017/0374074 | A1 | 12/2017 | Stuntebeck |
| 2018/0025351 | A1 | 1/2018 | Chen et al. |
| 2018/0025430 | A1 | 1/2018 | Perl et al. |
| 2018/0032126 | A1 | 2/2018 | Liu |
| 2018/0037228 | A1 | 2/2018 | Biondo et al. |
| 2018/0039303 | A1* | 2/2018 | Hashimoto ............. G02F 1/167 |
| 2018/0054513 | A1 | 2/2018 | Ma |
| 2018/0068105 | A1 | 3/2018 | Shapiro et al. |
| 2018/0093606 | A1 | 4/2018 | Terwilliger et al. |
| 2018/0115797 | A1 | 4/2018 | Wexler et al. |
| 2018/0120892 | A1 | 5/2018 | Von et al. |
| 2018/0123629 | A1 | 5/2018 | Wetzig |
| 2018/0167200 | A1 | 6/2018 | High et al. |
| 2018/0174457 | A1 | 6/2018 | Taylor |
| 2018/0292901 | A1 | 10/2018 | Priyantha et al. |
| 2018/0300467 | A1 | 10/2018 | Kwong et al. |
| 2019/0049267 | A1 | 2/2019 | Huang |
| 2019/0083022 | A1 | 3/2019 | Huang |
| 2019/0131812 | A1 | 5/2019 | Lee et al. |
| 2019/0155104 | A1 | 5/2019 | Li et al. |
| 2019/0191998 | A1 | 6/2019 | Heikenfeld et al. |
| 2019/0230507 | A1 | 7/2019 | Li et al. |
| 2019/0265868 | A1 | 8/2019 | Penilla et al. |
| 2019/0286805 | A1 | 9/2019 | Law et al. |
| 2019/0287083 | A1 | 9/2019 | Wurmfeld et al. |
| 2019/0298173 | A1 | 10/2019 | Lawrence et al. |
| 2019/0332140 | A1 | 10/2019 | Wang et al. |
| 2019/0342329 | A1 | 11/2019 | Turgeman |
| 2019/0357834 | A1 | 11/2019 | Aarts et al. |
| 2020/0005791 | A1 | 1/2020 | Rakshit et al. |
| 2020/0070840 | A1 | 3/2020 | Gunaratne |
| 2020/0218238 | A1 | 7/2020 | Wang |
| 2020/0356652 | A1 | 11/2020 | Yamaguchi et al. |
| 2020/0391696 | A1 | 12/2020 | Kato et al. |
| 2021/0197849 | A1* | 7/2021 | Tsuji .................... B60W 40/08 |
| 2021/0382684 | A1 | 12/2021 | Hachiya et al. |
| 2022/0083149 | A1 | 3/2022 | Keller et al. |

FOREIGN PATENT DOCUMENTS

| | | |
|---|---|---|
| CN | 206333477 U | 7/2017 |
| CN | 206371611 U | 8/2017 |
| CN | 107139933 A | 9/2017 |
| CN | 107260139 A | 10/2017 |
| CN | 108900691 A | 11/2018 |

(56) References Cited

FOREIGN PATENT DOCUMENTS

| CN | 108926081 A | 12/2018 |
|---|---|---|
| DE | 102015006677 A1 | 11/2016 |
| DE | 102019116618 A1 | 12/2020 |
| EP | 2581856 A1 | 4/2013 |
| KR | 10-2017-0087113 A | 7/2017 |
| WO | 2015/077418 A1 | 5/2015 |
| WO | 2017/136940 A1 | 8/2017 |
| WO | 2018/154341 A1 | 8/2018 |
| WO | 2018/204811 A1 | 11/2018 |
| WO | 2019/082095 A1 | 5/2019 |
| WO | 2019/140528 A1 | 7/2019 |
| WO | 2019/180626 A1 | 9/2019 |

OTHER PUBLICATIONS

"Vauxhall/Opel In-Car Wireless Charging", retrieved from <https://www.air-charge.com/aircharge-for-business/automotive/vauxhall-wireless- charging>, Oct. 2019, 4 pages.
"Wireless charging for smart ring/pointing devices" available online at <http://www.humavox.com/smt_product/wireless-charging-for-smart-ringpointing-devices/>, Oct. 2019, 3 pages.
ASU projection wearable: Live tomorrow today (world first launch @ CES 2016) (Dec. 2015) ASU Tech, YouTube. Retrieved from https://www.youtube.com/watch?v=Wdb5O-D7Y0Y.
Brownell, L., "Low-cost wearables manufactured by hybrid 3D printing. Wyss Institute, Harvard," Retrieved from https://wyss.harvard.edu/news/low-cost-wearables-manufactured-by-hybrid-3d-printing/, Sep. 6, 2017, pp. 11.
Cetin, C., "Design, testing and implementation of a new authentication method using multiple devices," Graduate Theses and Dissertations, University of South Florida Scholar Commons. Retrieved from http://scholarcommons.usf.edu/etd/5660, Jan. 2015, pp. 61.
Charles Q. Choi, "Low Battery? New Tech Lets You Wirelessly Share Power", available online at <https://www.livescience.com/54790-new-tech-enables-wireless-charging.html>, May 19, 2016, 9 pages.
Chen, X. A., et al., "Encore: 3D printed augmentation of everyday objects with printed-over, affixed and interlocked attachments," Nov. 5, 2015, pp. 73-82.
Chen, X. A., et al., "Reprise: A design tool for specifying, generating, and customizing 3D printable adaptations on everyday objects," Oct. 16, 2016, pp. 29-39.
E-Senses, "Personal vitamin D, sunlight and daylight coach", available online at <https://e-senses.com/>, 2019, 5 pages.
Hipolite, W., "The 3D printed Ö Bluetooth Ring is one of the tiniest personal computers you will ever see," 3DPrint.com. Retrieved from https://3dprint.com/34627/o-bluetooth-ring-3d-printed/, Jan. 2015, pp. 5.
Hussain Almossawi, "This smart ring aims to provide better lives for people with sickle cell disease", retrieved from <https://www.core77.com/projects/82131/This-Smart-Ring-Aims-to-Provide-Better-Lives-for-People-with-Sickle-Cell-Disease>, 2021, 9 pages.
Je et al., "PokeRing: Notifications by poking around the finger", Proceedings of the 2018 CHI Conference on Human Factors in Computing Systems—CHI'18, 2018, paper 542, pp. 1-10.
Katharine Schwab, "Orii, the ring that turns your finger into a phone, is here", available online at <https://www.fastcompany.com/90399237/orii-the-ring-that-turns-your-finger-into-a-phone-is-here >, 2019, 4 pages.
Magno et al., "Self-sustainable smart ring for long-term monitoring of blood oxygenation", IEEE Access, 2019, pp. 115400-115408.
Mahmud et al., "Wearable technology for drug abuse detection: A survey of recent advancements", Smart Health, vol. 13, Aug. 2019, 100062.
Margaret, "The Orb: A Bluetooth headset that turns into a ring", Gadgets, BornRich, Jun. 2013, available online at <http://www.bornrich.com/the-orb-a-bluetooth-headset-that-turns-into-a-ring.html >.
Nassi et al., "Virtual breathalyzer", Department of Software and Information Systems Engineering, Ben-Gurion University of the Negev, Israel, 2016, 10 pages.
Neev Kiran, "SkinnySensor: Enabling Battery-Less Wearable Sensors via Intrabody Power Transfer", Masters Theses 694, University of Massachusetts Amherst, 2018, 63 pages.
Nerd-Fu, "Push present", Delicious Juice Dot Com, Apr. 2015, available online at <https://blog.deliciousjuice.com/2015/04/ >.
Pablo E Suárez, "NXT Ring—Your Digital-self at Hand", available online at <https://www.youtube.com/watch?v=9w7uxDHs7NY>, uploaded on Jun. 21, 2019, 2 pages.
Roumen et al., "NotiRing: A comparative study of notification channels for wearable interactive rings", Proceedings of the 33rd Annual ACM Conference on Human Factors in Computing Systems—CHI'15, 2015, pp. 2497-2500.
Sarah Jacobsson Purewal, "Ringly review: The smart ring that could be sexier", available online at <https://www.macworld.com/article/227133/ringly-review-the-smart-ring-that-could-be-sexier.html>, 2016, 10 pages.
Schwab, K., "This startup wants to kill passwords—and replace them with jewelry. Fast Company," Retrieved from https://www.fastcompany.com/90254843/this-startup-wants-to-kill-passwords-and-replace-them-with-jewelry, (Oct. 2018), pp. 7.
Seung et al., "Nanopatterned Textile-Based Wearable Triboelectric Nanogenerator", ACS Nano, vol. 9, 2015, pp. 3501-3509.
Shane McGlaun, "Geek builds Bluetooth Smart Ring with OLED display", available online at <https://www.slashgear.com/geek-builds-bluetooth-smart-ring-with-oled-display-02361383/>, 2015, 6 pages.
Sperlazza, "We tested four sleep tracker apps and wearables: Here are the best ones", available online at <https://www.bulletproof.com/sleep/tech/best-sleep-tracker-apps/>, 2019, 18 pages.
Turunen, "Smart ring for stress control and self-understanding", available online at <https://slowfinland.fi/en/smart-ring-for-stress-control-and-self-understanding/>, 2017, 9 pages.
Wochit Tech. (2017). New smart ring monitors UV exposure [Video file]. Retrieved from https://www.youtube.com/watch?v=4YvkioTZxjU, 3 pages.
Worgan et al., "Garment level power distribution for wearables using inductive power transfer", 9th International Conference on Human System Interactions (HSI), 2016, pp. 277-283.
Xiao et al., "LumiWatch: On-arm projected graphics and touch input", Proceedings of the 2018 CHI Conference on Human Factors in Computing Systems—CHI'18, 2018, pp. 1-11.
Zhu et al., "Developing a driving fatigue detection system using physiological sensors", Proceedings of the 29th Australian Conference on Computer-Human Interaction—OZCHI '17, 2017, pp. 566-570.
Zhu, M. et al. "Fluidic fabric muscle sheets for wearable and soft robotics," Retrieved from https://arxiv.org/pdf/1903.08253.pdf, Mar. 2019, pp. 32.
Adafruit, p. 1-2, available at: https://www.adafruit.com/product/2806, published Jun. 2019 (Year: 2019).
https://en.wikipedia.org/w/index.php?title=Ring_size&oldid=891328817 (Year: 2019).
Laput et al., "Skin buttons: cheap, small, low-powered and clickable fixed-icon laser projectors", UIST '14: Proceedings of the 27th annual ACM symposium on User interface software and technology, Oct. 2014 pp. 389-394.
Mario, https://www.smartringnews.com/posts/smart-ring-vs-smartwatch-which-is-the-best-fitness-and-activity-tracker (Year: 2014).
Google translation of KR20170087113A (Year: 2016).

* cited by examiner

ELECTRONIC INK DISPLAY FOR SMART RING

CROSS-REFERENCES TO RELATED APPLICATIONS

This application claims priority to U.S. Provisional Patent Application No. 62/877,391, filed Jul. 23, 2019, and U.S. Provisional Patent Application No. 62/981,089, filed Feb. 25, 2020, both incorporated by reference herein for all purposes.

FIELD OF THE DISCLOSURE

The present disclosure generally relates to implementations of smart ring wearable devices and, more particularly, to methods and devices for displaying information indicative of driving conditions to a driver via electronic-in ("e-ink") smart ring wearable devices.

BACKGROUND

Information pertaining to driving conditions of a vehicle and/or driver are valuable for navigation of the vehicle, ensuring safe operation of the vehicle, and lawful operation of the vehicle. Typically, operators of vehicles are provided, via a console display within the vehicle, with a limited amount of information pertaining to the vehicle (such as a speed of the vehicle or operational statuses of various elements of the vehicle such as the motor, oil levels, heat levels, etc.). In typical vehicles, information provided by the vehicle to an operator of a vehicle is typically limited to the operational statuses of the vehicle itself.

BRIEF SUMMARY

As disclosed herein, a smart ring device is configured for displaying information indicative of driving conditions to a driver via an e-ink display (sometimes simply referred to herein as a "display"). The smart ring device allows for the presentation of a multitude of different factors and conditions to a driver of a vehicle (e.g., a wearer of the smart ring) during operation of a vehicle. One benefit of the smart ring device is that the smart ring may measure biometrics of the driver and display indications of the biometrics such as a heart rate, blood pressure, blood-oxygen level, etc. Further, based at least in part upon the biometric information, the smart ring may provide indications to a driver of an operational state of the driver (e.g., a weariness level of a driver, an inebriation level, etc.) to indicate a potential risk of hazardous driving of the driver. The smart ring may be easily worn by a user of the smart ring throughout the user's day, and/or overnight, allowing the smart ring to track sleeping habits and physical exertion allowing for the smart ring to more accurately determine physical states of the wearer of the smart ring, compared to other user associated cellular devices such as a cell phone or step tracker. Additionally, the smart ring may display to a driver indications of environmental conditions, operating conditions of the vehicle, conditions of other drivers, conditions of other vehicles, or may display driving risk levels based at least in part upon any of the conditions, or combinations of conditions.

Conventional vehicle console displays are large and need a driver to gaze at the console to observe information presented by the console, or to make selections on the console, which could be hazardous when driving in certain conditions (e.g., congested traffic, during rain or inclement weather, along a ridge or mountainside, etc.) Additionally, cellular devices, such as cell phones or tablets, associated with a user needs the driver to look at the screen or operate the device, which is illegal in some regions. The smart ring device can provide indications to a driver without the driver having to remove any hands from a steering wheel of the vehicle, or having to shift their gaze to a central console, which can reduce the risk of hazardous driving, and/or unlawful driving. Additionally, the display methods of the smart ring device have low-power needs compared to conventional display technologies.

This summary is provided to introduce a selection of concepts that are further described below in the detailed description. Certain embodiments may include features and advantages not described in this summary. Further, certain embodiments may omit one or more (or all) of the features and advantages described in this summary.

In an embodiment, a system for displaying information indicative of driving conditions to a driver via a smart ring device includes a ring band having a plurality of surfaces including an inner surface, an outer surface, a first side surface, and a second side surface. The smart ring further includes a processor, configured to obtain data from a communication module disposed within the ring band or from one or more sensors disposed within the ring band, the data being representative of information indicative of the one or more driving conditions. The smart ring also includes an e-ink display disposed on at least one of the plurality of surfaces, configured to present, to a user of the smart ring device, information indicative of one or more driving conditions.

The system may further include a power source disposed within the ring band configured to power the smart ring device, and a memory to store computer-executable instructions. The computer executable instructions may cause the processor to obtain information indicative of the one or more driving conditions, and to control the e-ink display to cause the e-ink display to display visual indicia indicative of the one or more driving conditions.

The communication module may be configured to provide communications between the smart ring device and external devices and systems. The smart ring device may communicate, via the communication module, with a mobile device associated with the driver of a vehicle, wherein the mobile device is configured to obtain information from sensors of the vehicle.

The system may further include a user input unit communicatively coupled to the processor. The user input unit may include haptic sensors, microphones, or other sensors to enable a user to provide a user input to the user input unit. The processor may further be configured to cause the e-ink display to present the information indicative of the identified one or more driving conditions within a selected portion of the e-ink display in response to receiving a user input representing a selection of the selected portion. The processor may further be configured to initiate scrolling of the information indicative of the identified one or more driving conditions upon receiving a user input, halt the scrolling of the information upon receiving a user input, increase the scrolling speed of the information upon receiving a user input, or decrease the scrolling speed of the information upon receiving a user input.

The system may further include biometric sensors configured to monitor biometrics of the wearer of the smart ring, and further configured to communicate, via the communication module, biometric information to a mobile device associated with the driver of the vehicle.

The information indicative of driving conditions may be indicative of a speed of a vehicle, an acceleration of a vehicle, a current weather condition, a sleepiness condition of a driver, a cognoscente condition of a driver, an inebriation condition of a driver, an operational status of a vehicle, and/or biometric information of a wearer of the smart ring device.

Depending upon the embodiment, one or more benefits may be achieved. These benefits and various additional objects, features and advantages of the present disclosure can be fully appreciated with reference to the detailed description and accompanying drawings that follow.

DETAILED DESCRIPTION

Figure 1:
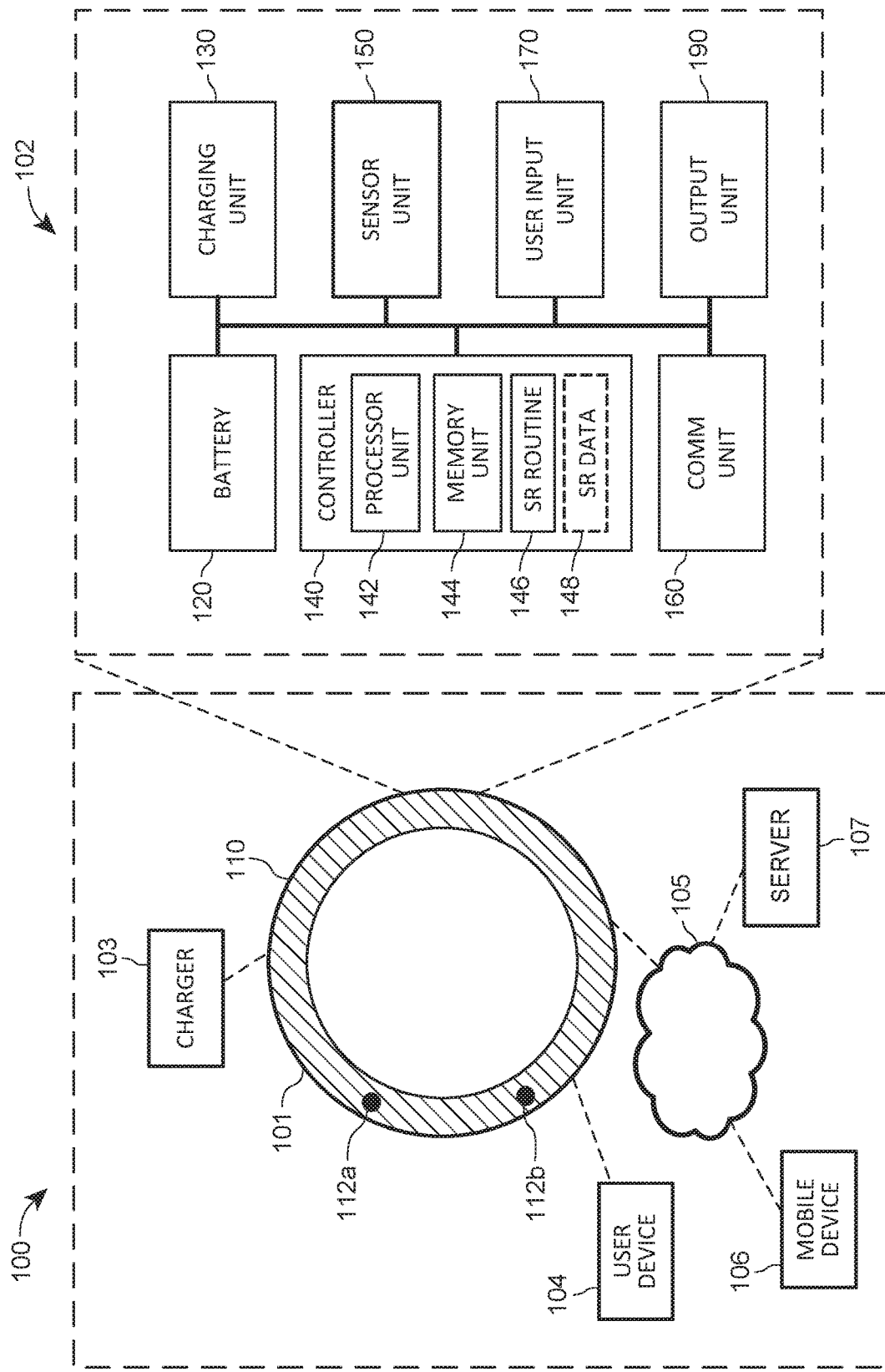
FIG. 1 illustrates a system comprising a smart ring and a block diagram of smart ring components according to some embodiments.
Figure 2:
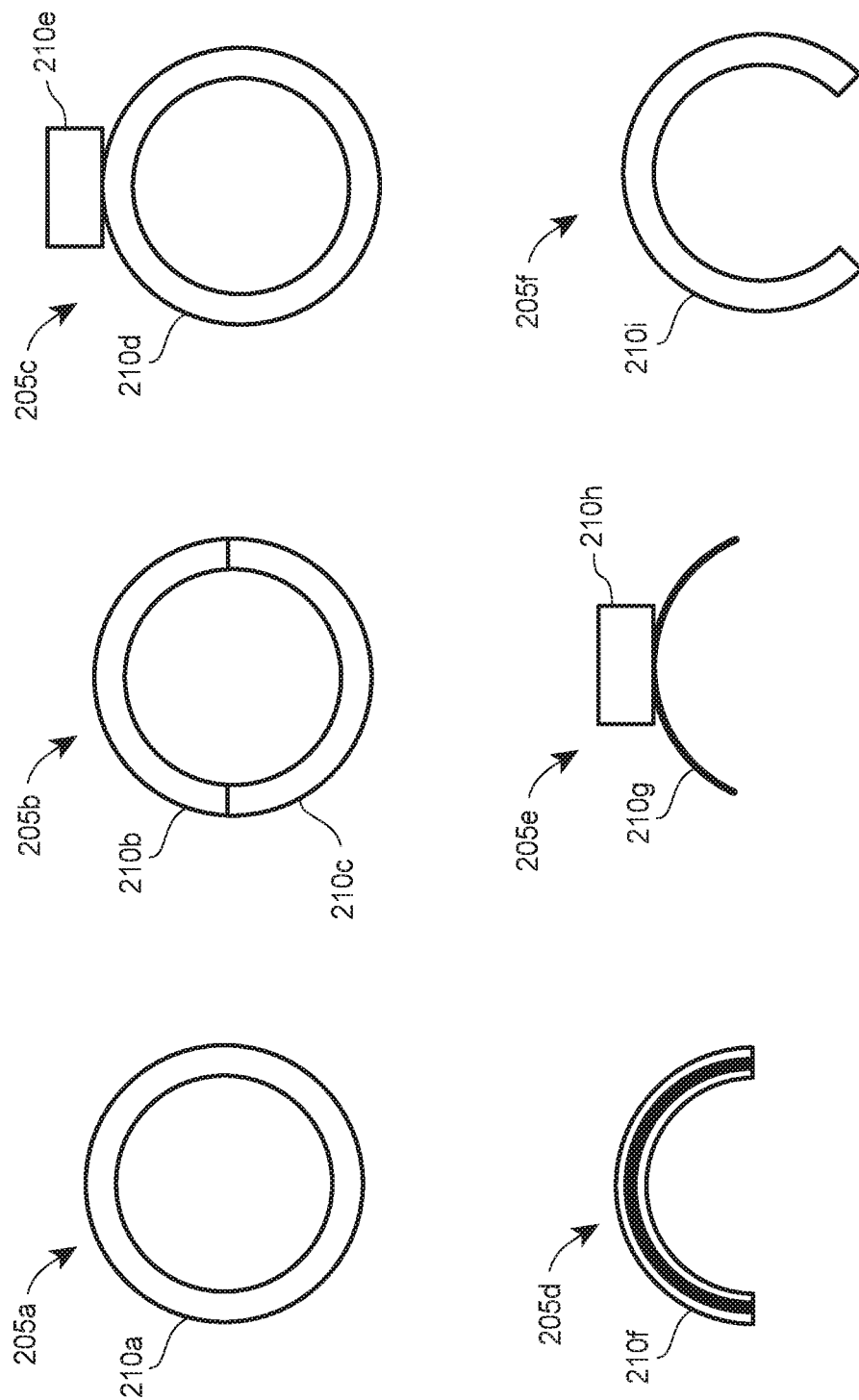
FIG. 2 illustrates a number of different form factor types of a smart ring according to some embodiments.
Figure 3:
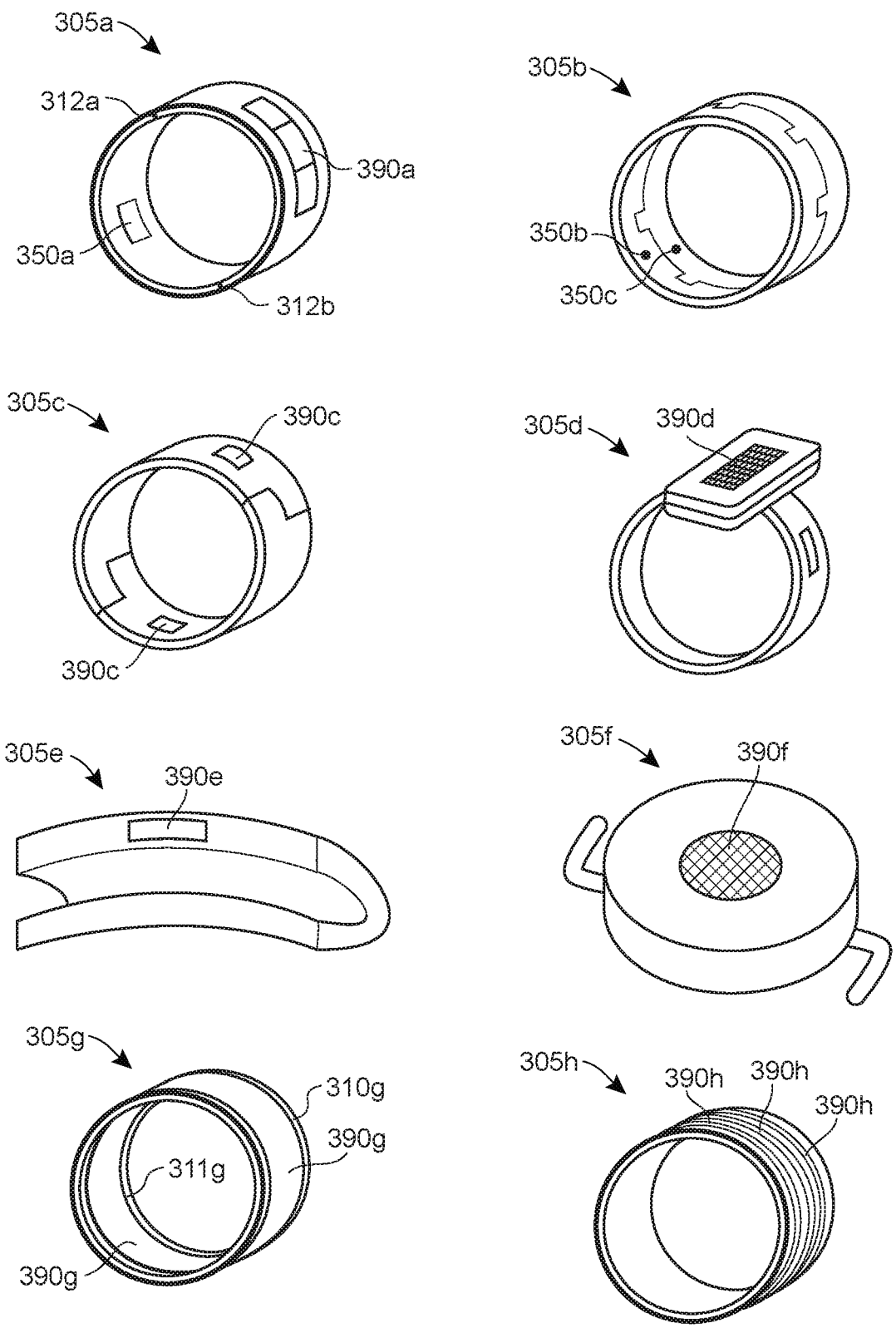
FIG. 3 illustrates examples of different smart ring form factors and configurations according to some embodiments.
Figure 4A:
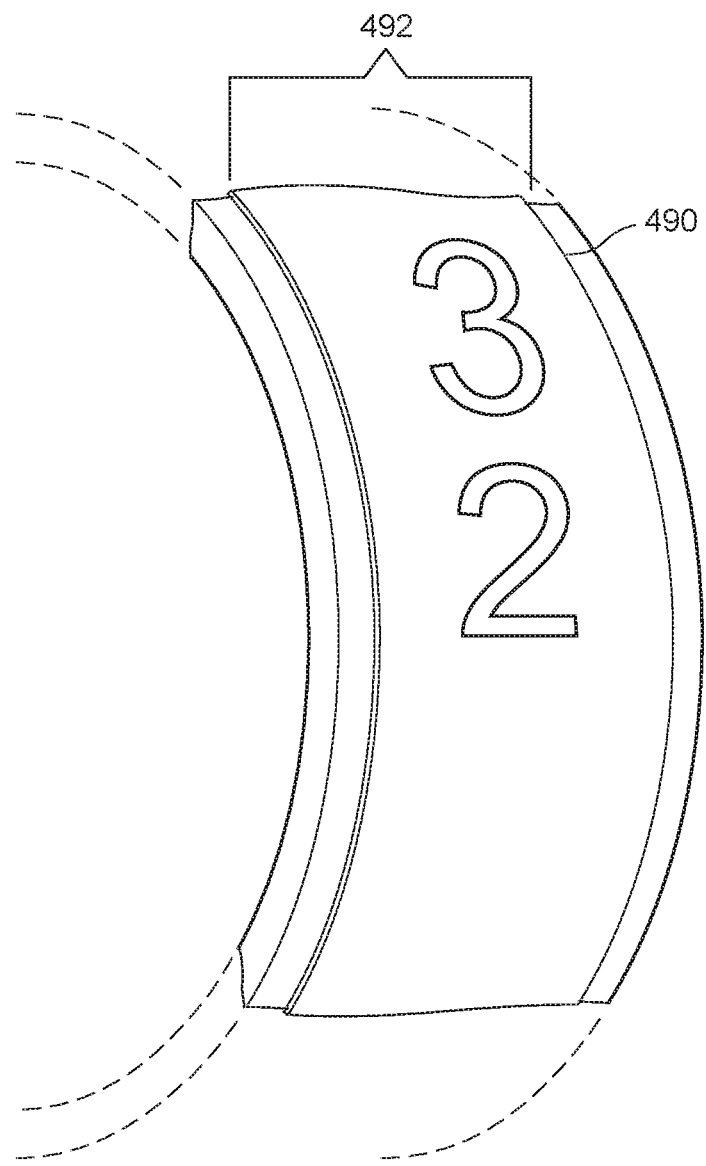
FIG. 4A is an illustration of an output device with an e-ink display for displaying characters and symbols according to some embodiments.
Figure 4B:
FIG. 4B and FIG. 4C illustrate the scrolling of a message across an e-ink display of an output device according to some embodiments.
Figure 4C:
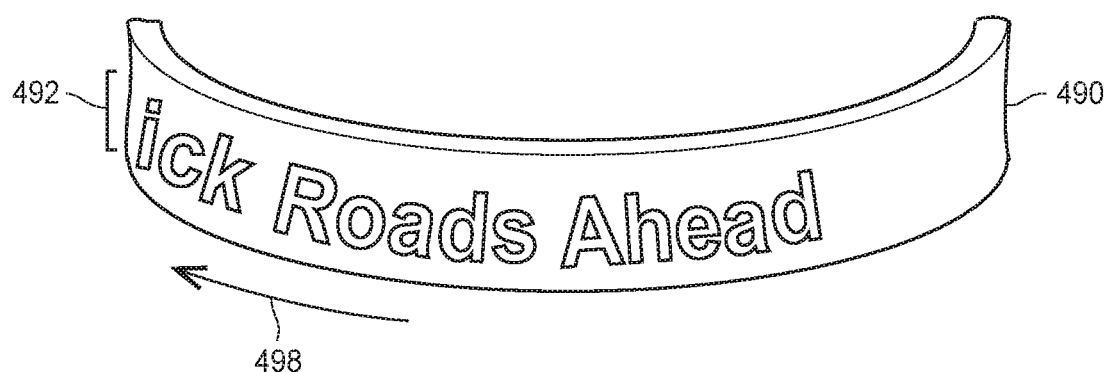
Figure 5:
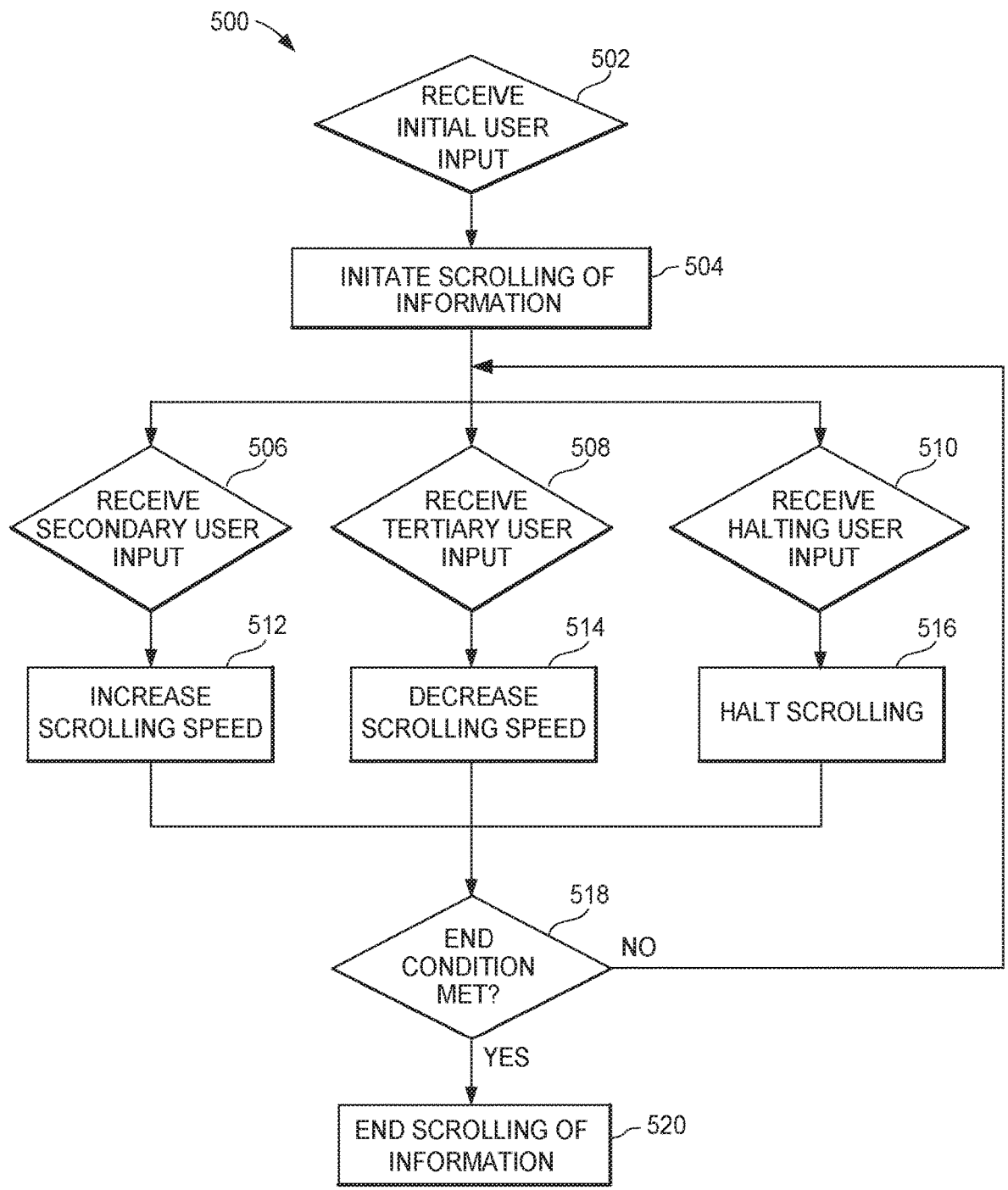
FIG. 5 flow diagram of a method for controlling the scrolling of information across an output device, such as an e-ink display, of a smart ring according to some embodiments.
Figure 6:
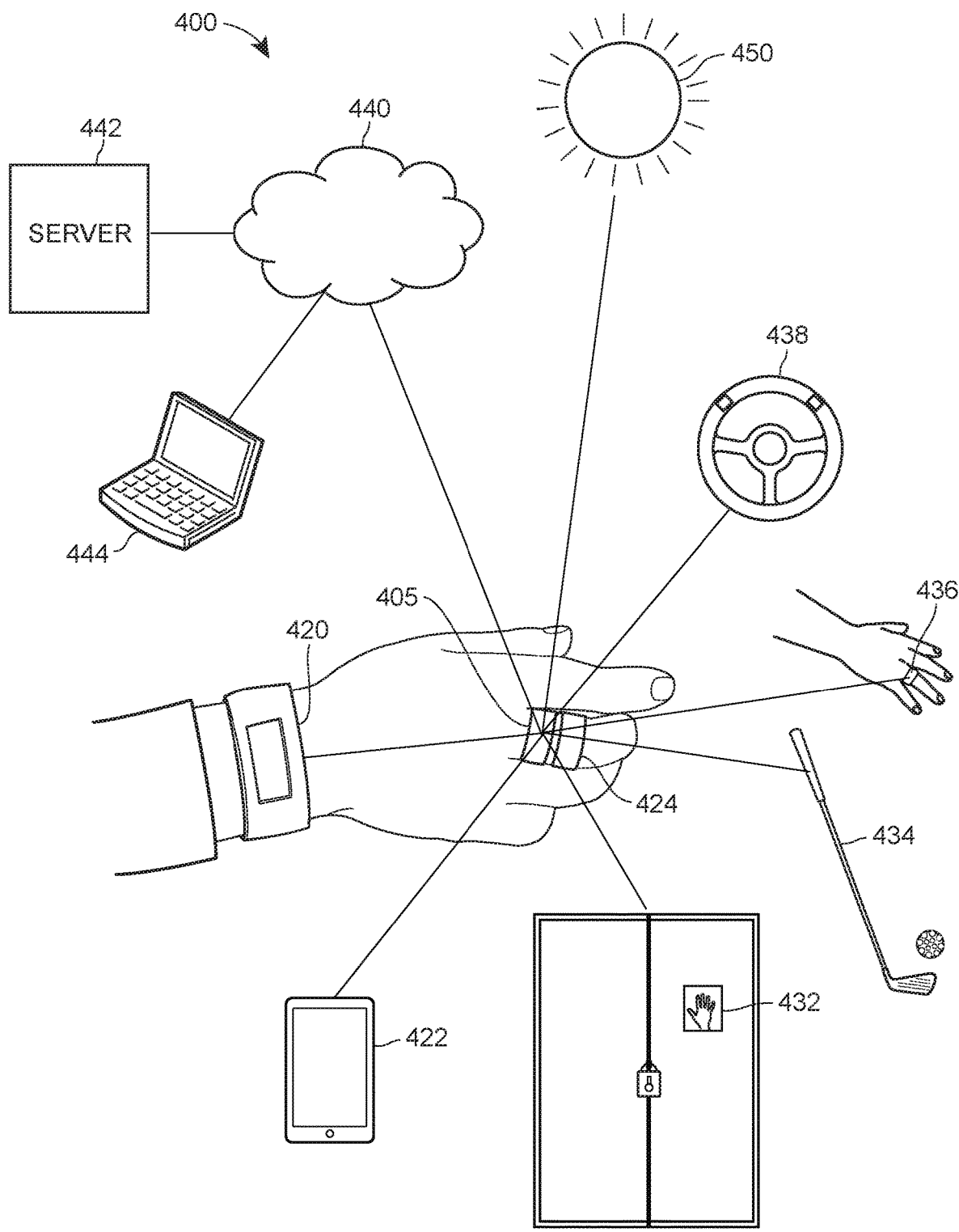
FIG. 6 illustrates an environment within which a smart ring may operate according to some embodiments.

Various techniques, systems, and methods are described below with reference to FIG. 1, FIG. 2, FIG. 3, FIG. 4, FIG. 5, and FIG. 6. FIG. 1 and FIG. 6 illustrate example systems and system components that incorporate a smart ring. FIG. 2 and FIG. 3 depict various form factors and configurations of smart ring embodiments. FIG. 4A, FIG. 4B, and FIG. 4C depict smart ring devices with e-ink displays for displaying information. FIG. 5 illustrates a method of controlling the scrolling of information across an e-ink display of a smart ring device.

Specifically, the following is described: (I) an example smart ring system 100 (shown in FIG. 1), configured to present information indicative of driving conditions to a driver of a vehicle, including a smart ring 101, a set of smart ring components 102, and one or more devices or systems in communication with the smart ring including a user device 104, a mobile device 106, and a server 107; (II) smart ring form factor types of the smart ring 101 (FIG. 2); (III) example surface element configurations of the smart ring form factor types of the smart ring 101 (FIG. 3); (IV) examples of smart ring configurations with e-ink displays as output devices (FIG. 3); (V) smart ring examples with e-ink displays for displaying characters and symbols (FIG. 4A, FIG. 4B, FIG. 4C, and FIG. 5); (VI) an example environment 400 in which smart ring 101 may operate (FIG. 6), including (1) server 442 and (2) other sample devices; (IX) additional considerations; and (X) general terms and phrases.

The "driving conditions" identified by the smart ring or communicated by the smart ring to a user of the smart ring may be: (i) biometrics of a user of the smart ring including, without limitation, pulse rate, blood flow, blood oxygen level, blood pressure, skin salinity level, temperature, weariness level, a cognoscente condition of the user, an inebriation condition of the user, or any other biological and biometric information; (ii) a state of a user such as erratic behavior of the user, sleepiness of the user, or a stress level of the user; (iii) detected vehicular statuses such as engine temperature, oil level, a needed oil change, coolant level, exhaust fume legal compliance, break pad health, low battery charge, flat tire, alternator failure, tire alignment/misalignment, transmission issue, power steering fluid level, brake fluid level, transmission fluid level, windshield wiper fluid level, etc.; (iv) vehicular operations such as a speed of a vehicle, an acceleration of a vehicle, a current altitude of the vehicle, a lane centering of the vehicle, a fuel efficiency of the vehicle, an autopilot function status of the vehicle (e.g., autopilot is activated/not-activated), an operational of autonomous driving function of the vehicle is deactivated, an autonomous driving function of the vehicle is activated, air bags are activated/de-activated, a seat belt is latched/unlatched, a temperature of the environment inside of the cabin of the vehicle, etc.; external factors or environmental factors such as current or predicated weather conditions (e.g., rain, snow, extreme heat, etc.), current external environmental conditions (e.g., wet/slick roads, fog levels, a visibility level, dangerous breathing air, external temperature, etc.), current conditions inside of the cab of the vehicle (e.g., the temperature, air quality, moisture level, etc.); information and statuses of nearby vehicles, identifications that a nearby driver is driving erratically; driving conditions during operation of a vehicle such as the congestion of drivers along a road or planned trip route, the current proximity of the vehicle to external objects outside of the vehicle (e.g., other vehicles, pedestrians, trees, etc.), or other factors associated with operation of a vehicle; or another element or factor that may have an influence or impact of the operation of a vehicle.

The "data" that is received by a processor of the smart ring (via a sensor or communication module of the smart ring) and analyzed by the processor to identify the one or more driving conditions may include: biometric data of a wearer of the smart ring (e.g., representing detect heart beats, perspiration, user movement, etc.), biometric data from a user associated device, data from sensors of the vehicle (e.g., speed data, direction data, laser or camera data representing captured information regarding environmental or road conditions), data from a central console of the vehicle, data from sensors of other vehicles, data from central consoles of other vehicles, data from user associated devices or drivers from other vehicles, data from a network, data associated with a driving history of a driver, data associated with a health history of a driver, data associated with behavior trends of a driver, or data indicative of any of the driving conditions described above.

The "e-ink" display of the smart rings described herein may be any suitable e-ink display. E-ink displays may also be referred to as e-paper or an e-paper display. In examples, the e-ink display may be a color e-ink display, a black and white e-ink display, a segmented e-ink display, a matrix e-ink display, or another type of e-ink display. E-ink technologies are reflective displays which need no backlight to illuminate the display, which reduces the energy needed and increases battery life of batteries for powering e-ink displays. Additionally, the reflective display technologies reduce eye fatigue for users. Images displayed on e-ink devices are retained without additional power consumption, and therefore power is only needed when information, or images are changing on an e-ink display, further reducing power consumption and increasing battery life when compared to other display technologies (e.g., LEDs, LCD displays, etc.). E-ink displays may be fabricated using glass or plastic based thin-film transistors (TFTs). Plastic-based TFT displays are substantially lighter and may have smaller form factors than glass based TFT displays. Additionally, the plastic based TFT e-ink displays are typically less sensitive to impact and are more durable than glass-based TFT counterparts. E-ink displays may be beneficial for use in smart ring technologies because of the low-power consumption, capability for small form factors, and durability of the displays, among other factors, as described above.

I. An Example Smart Ring Environment

FIG. 1 illustrates a system 100 that may be utilized to display relevant information to a driver, thereby improving the driver's awareness of the state of the vehicle, environment, and even his or her own state and consequently improving the driver's safety profile and reducing his or her risk exposure while driving. The system 100 may obtain information indicative of driving conditions as described herein to display information indicative of the driving conditions to the driver of the vehicle.

The system 100 comprises (i) a smart ring 101 including a set of components 102 and (ii) one or more devices or systems that may be electrically, mechanically, or communicatively connected to the smart ring 101. Specifically, the system 100 may comprise any one or more of: a charger 103 for the smart ring 101, a user device 104, a network 105, a mobile device 106, or a server 107. The charger 103 may provide energy to the smart ring 101 by way of a direct electrical, a wireless, or an optical connection. The smart ring 101 may be in a direct communicative connection with the user device 104, the mobile device 106, or the server 107 by way of the network 105. Interactions between the smart ring 101 and other components of the system 100 are discussed in more detail in the context of FIG. 6.

The smart ring 101 may sense a variety of signals indicative of activities of a user wearing the ring 101, biometric signals, a physiological state of the user, or signals indicative of the user's environment. The smart ring 101 may analyze the sensed signals using built-in computing capabilities or in cooperation with other computing devices (e.g., user device 104, mobile device 106, server 107) and provide feedback to the user or about the user via the smart ring 101 or other devices (e.g., user device 104, mobile device 106, server 107). The smart ring 101 may process the sensed signals and provide visual outputs to the user of the smart ring 101 indicative of any of the sensed signals, as discussed further below. Additionally or alternatively, the smart ring 101 may provide the user with notifications sent by other devices, enable secure access to locations or information, or a variety of other applications pertaining to health, wellness, productivity, or entertainment.

The smart ring 101, which may be referred to herein as the ring 101, may comprise a variety of mechanical, electrical, optical, or any other suitable subsystems, devices, components, or parts disposed within, at, throughout, or in mechanical connection to a housing 110 (which may be ring shaped and generally configured to be worn on a finger). Additionally, a set of interface components 112a and 112b may be disposed at the housing, and, in particular, through the surface of the housing. The interface components 112a and 112b may provide a physical access (e.g., electrical, fluidic, mechanical, or optical) to the components disposed within the housing. The interface components 112a and 112b may exemplify surface elements disposed at the housing. As discussed below, some of the surface elements of the housing may also be parts of the smart ring components.

As shown in FIG. 1, the components 102 of the smart ring 101 may be distributed within, throughout, or on the housing 110. As discussed in the contexts of FIG. 2 and FIG. 3 below, the housing 110 may be configured in a variety of ways and include multiple parts. The smart ring components 102 may, for example, be distributed among the different parts of the housing 110, as described below, and may include surface elements of the housing 110. The housing 110 may include mechanical, electrical, optical, or any other suitable subsystems, devices, components, or parts disposed within or in mechanical connection to the housing 110, including a battery 120, a charging unit 130, a controller 140, a sensor system 150 comprising one or more sensors, a communications unit 160, a one or more user input devices 170, or a one or more output devices 190. Each of the components 120, 130, 140, 150, 160, 170, and/or 190 may include one or more associated circuits, as well as packaging elements. The components 120, 130, 140, 150, 160, 170, and/or 190 may be electrically or communicatively connected with each other (e.g., via one or more busses or links, power lines, etc.), and may cooperate to enable "smart" functionality described within this disclosure.

The battery 120 may supply energy or power to the controller 140, the sensors 150, the communications unit 160, the user input devices 170, or the output devices 190. In some scenarios or implementations, the battery 120 may supply energy or power to the charging unit 130. The charging unit 130 may supply energy or power to the battery 120. In some implementations, the charging unit 130 may supply (e.g., from the charger 103, or harvested from other sources) energy or power to the controller 140, the sensors 150, the communications unit 160, the user input devices 170, or the output devices 190. In a charging mode of operation of the smart ring 101, the average power supplied by the charging unit 130 to the battery 120 may exceed the average power supplied by the battery 120 to the charging unit 130, resulting in a net transfer of energy from the charging unit 130 to the battery 120. In a non-charging mode of operation, the charging unit 130 may, on average, draw energy from the battery 120.

The battery 120 may include one or more cells that convert chemical, thermal, nuclear or another suitable form of energy into electrical energy to power other components or subsystems 140, 150, 160, 170, and/or 190 of the smart ring 101. The battery 120 may include one or more alkaline, lithium, lithium-ion and or other suitable cells. The battery 120 may include two terminals that, in operation, maintain a substantially fixed voltage of 1.5, 3, 4.5, 6, 9, 12 V or any other suitable terminal voltage between them. When fully charged, the battery 120 may be capable of delivering to power-sinking components an amount of charge, referred to herein as "full charge," without recharging. The full charge of the battery may be 1, 2, 5, 10, 20, 50, 100, 200, 500, 1000, 2000, 5000, 10000, 20000 mAh or any other suitable charge that can be delivered to one or more power-consuming loads as electrical current.

The battery 120 may include a charge-storage device, such as, for example a capacitor or a super-capacitor. In some implementations discussed below, the battery 120 may be entirely composed of one or more capacitive or charge-storage elements. The charge storage device may be capable of delivering higher currents than the energy-conversion cells included in the battery 120. Furthermore, the charge storage device may maintain voltage available to the components or subsystems 130, 140, 150, 160, 170, and/or 190 when one or more cells of the battery 120 are removed to be subsequently replaced by other cells.

The charging unit 130 may be configured to replenish the charge supplied by the battery 120 to power-sinking components or subsystems (e.g., one or more of subsystems 130, 140, 150, 160, 170, and/or 190) or, more specifically, by their associated circuits. To replenish the battery charge, the charging unit 130 may convert one form of electrical energy into another form of electrical energy. More specifically, the charging unit 130 may convert alternating current (AC) to direct current (DC), may perform frequency conversions of current or voltage waveforms, or may convert energy stored in static electric fields or static magnetic fields into direct current. Additionally or alternatively, the charging unit 130 may harvest energy from radiating or evanescent electromagnetic fields (including optical radiation) and convert it into the charge stored in the battery 120. Furthermore, the charging unit 130 may convert non-electrical energy into electrical energy. For example, the charging unit 130 may harvest energy from motion, or from thermal gradients.

The controller 140 may include a processor unit 142 and a memory unit 144. The processor unit 142 may include one or more processors, such as a microprocessor (μP), a digital signal processor (DSP), a central processing unit (CPU), a graphical processing unit (GPU), a field-programmable gate array (FPGA), an application-specific integrated circuit (ASIC), or any other suitable electronic processing components. In embodiments, the controller may include a dedicated graphics-processing unit (GPU) for rendering images, animations, characters, symbols, or any visual outputs to be presented to the user of the smart ring 101. Additionally or alternatively, the processor unit 142 may include photonic processing components (e.g., cameras, optical sensors, waveguide, optical storage, optical switches, light emitting diodes (LEDs) laser diode (LDs), etc.).

The memory unit 144 may include one or more computer memory devices or components, such as one or more registers, RAM, ROM, EEPROM, or on-board flash memory. The memory unit 144 may use magnetic, optical, electronic, spintronic, or any other suitable storage technology. In some implementations, at least some of the functionality the memory unit 144 may be integrated in an ASIC or and FPGA. Furthermore, the memory unit 144 may be integrated into the same chip as the processor unit 142 and the chip, in some implementations, may be an ASIC or an FPGA.

The memory unit 144 may store a smart ring (SR) routine 146 with a set of instructions, that, when executed by the processor 142 may enable the operation and the functionality described in more detail below. Furthermore, the memory unit 144 may store smart ring (SR) data 148, which may include (i) input data used by one or more of the components 102 (e.g., by the controller when implementing the SR routine 146) or (ii) output data generated by one or more of the components 102 (e.g., the controller 140, the sensor unit 150, the communication unit 160, or the user input unit 170). In some implementations, other units, components, or devices may generate data (e.g., diagnostic data) for storing in the memory unit 144.

The processing unit 142 may draw power from the battery 120 (or directly from the charging unit 130) to read from the memory unit 144 and to execute instructions contained in the smart ring routine 146. Likewise, the memory unit 144 may draw power from the battery 120 (or directly from the charging unit 130) to maintain the stored data or to enable reading or writing data into the memory unit 144. The processor unit 142, the memory unit 144, or the controller 140 as a whole may be capable of operating in one or more low-power mode. One such low power mode may maintain the machine state of the controller 140 when less than a threshold power is available from the battery 120 or during a charging operation in which one or more battery cells are exchanged.

The controller 140 may receive and process data from the sensors 150, the communications unit 160, or the user input devices 170. The controller 140 may perform computations to generate new data, signals, or information. The controller 140 may send data from the memory unit 144 or the generated data to the communication unit 160 or the output devices 190. The electrical signals or waveforms generated by the controller 140 may include digital or analog signals or waveforms. The controller 140 may include electrical or electronic circuits for detecting, transforming (e.g., linearly or non-linearly filtering, amplifying, attenuating), or converting (e.g., digital to analog, analog to digital, rectifying, changing frequency) of analog or digital electrical signals or waveforms.

The sensor unit 150 may include one or more sensors disposed within or throughout the housing 110 of the ring 101. Each of the one or more sensors may transduce one or more of: light, sound, acceleration, translational or rotational movement, strain, temperature, chemical composition, surface conductivity, pressure, or other suitable signals into electrical or electronic sensors or signals. A sensor may be acoustic, photonic, micro-electro-mechanical systems (MEMS) sensors, chemical, micro-fluidic (e.g., flow sensor), or any other suitable type of sensor. The sensor unit 150 may include, for example, an inertial motion unit (IMU) for detecting orientation and movement of the ring 101.

The communication unit 160 may facilitate wired or wireless communication between the ring 101 and one or more other devices. The communication unit 160 may include, for example, a network adaptor to connect to a computer network, and, via the network, to network-connected devices. The computer network may be the Internet or another type of suitable network (e.g., a personal area network (PAN), a local area network (LAN), a metropolitan area network (MAN), a wide area network (WAN), a mobile, a wired or wireless network, a private network, a virtual private network, etc.). The communication unit 160 may use one or more wireless protocols, standards, or technologies for communication, such as Wi-Fi, near field communication (NFC), Bluetooth, or Bluetooth low energy (BLE). Additionally or alternatively, the communication unit 160 may enable free-space optical or acoustic links. In some implementations, the communication unit 160 may include one or more ports for a wired communication connections. The wired connections used by the wireless communication module 160 may include electrical or optical connections (e.g., fiber-optic, twisted-pair, coaxial cable).

User input unit 170 may collect information from a person wearing the ring 101 or another user, capable of interacting with the ring 101. In some implementations, one or more of the sensors in the sensor unit 150 may act as user input devices within the user input unit 170. User input devices may transduce tactile, acoustic, video, gesture, or any other suitable user input into digital or analog electrical signal, and send these electrical signals to the controller 140.

The output unit 190 may include one or more devices to output information to a user of the ring 101. The one or more output devices may include acoustic devices (e.g., speaker, ultrasonic); haptic (thermal, electrical) devices; electronic displays for optical output, such as an organic light emitting device (OLED) display, a laser unit, a high-power light-emitting device (LED), etc.; an e-ink display (e.g., a segmented e-ink display, a matrix e-ink display, a color e-ink display, etc.), or any other suitable types of devices. For example, the output unit 190 may include a projector that projects an image onto a suitable surface. In some implementations, the sensor unit 150, the user input unit 170, and the output unit 190 may cooperate to create a user interface with capabilities (e.g., a keyboard) of much larger computer systems, as described in more detail below.

The components 120, 130, 140, 150, 160, 170, and/or 190 may be interconnected by a bus 195, which may be implemented using one or more circuit board traces, wires, or other electrical, optoelectronic, or optical connections. The bus 195 may be a collection of electrical power or communicative interconnections. The communicative interconnections may be configured to carry signals that conform to any one or more of a variety of protocols, such as I2C, SPI, or other logic to enable cooperation of the various components.

II. Example Form Factor Types for a Smart Ring

FIG. 2 includes block diagrams of a number of different example form factor types or configurations 205a, 205b, 205c, 205d, 205e, and/or 205f of a smart ring (e.g., the smart ring 101) that may be utilized to display information indicative of driving conditions to a driver, thereby improving the driver's awareness of the state of the vehicle, environment, and even his or her own state and consequently improving the driver's safety profile and reducing his or her risk exposure while driving. The system configurations 205a, 205b, 205c, 205d, 205e, and/or 205f may obtain information indicative of the driving conditions via sensors disposed on/or within the configurations, or from communicating with external devices.

The configurations 205a, 205b, 205c, 205d, 205e, and/or 205f (which may also be referred to as the smart rings 205a, 205b, 205c, 205d, 205e, and/or 205f) may each represent an implementation of the smart ring 101, and each may include any one or more of the components 102 (or components similar to the components 102). In some embodiments, one or more of the components 102 may not be included in the configurations 205a, 205b, 205c, 205d, 205e, and/or 205f. The configurations 205a, 205b, 205c, 205d, 205e, and/or 205f include housings 210a, 210b, 210c, 210d, 210e, and/or 210f, which may be similar to the housing 110 shown in FIG. 1.

The configuration 205a may be referred to as a band-only configuration comprising a housing 210a. In the configuration 205b, a band may include two or more removably connected parts, such as the housing parts 210b and 210c. The two housing parts 210b and 210c may each house at least some of the components 102, distributed between the housing parks 210b and 210c in any suitable manner.

The configuration 205c may be referred to as a band-and-platform configuration comprising (i) a housing component 210d and (ii) a housing component 210e (sometimes called the "platform 210e"), which may be in a fixed or removable mechanical connection with the housing 210d. The platform 210e may function as a mount for a "jewel" or for any other suitable attachment. The housing component 210d and the platform 210e may each house at least one or more of the components 102 (or similar components).

In some instances, the term "smart ring" may refer to a partial ring that houses one or more components (e.g., components 102) that enable the smart ring functionality described herein. The configurations 205d and 205e may be characterized as "partial" smart rings, and may be configured for attachment to a second ring. The second ring may be a conventional ring without smart functionality, or may be second smart ring, wherein some smart functionality of the first or second rings may be enhanced by the attachment.

The configuration 205d, for example, may include a housing 210f with a groove to enable clipping onto a conventional ring. The grooved clip-on housing 210f may house the smart ring components described above. The configuration 205e may clip onto a conventional ring using a substantially flat clip 210g part of the housing and contain the smart ring components in a platform 210h part of the housing.

The configuration 205f, on the other hand, may be configured to be capable of being mounted onto a finger of a user without additional support (e.g., another ring). To that end, the housing 210i of the configuration 205f may be substantially of a partial annular shape subtending between 180 and 360 degrees of a full circumference. When implemented as a partial annular shape, the housing 210i may be more adaptable to fingers of different sizes that a fully annular band (360 degrees), and may be elastic. A restorative force produced by a deformation of the housing 210i may ensure a suitable physical contact with the finger. Additional suitable combinations of configurations (not illustrated) may combine at least some of the housing features discussed above.

III. Example Surface Elements of a Smart Ring

FIG. 3 includes perspective views of example configurations 305a, 305b, 305c, 305d, 305e, 305f, 305g, and/or 305h of a smart right (e.g., the smart ring 101) in which a number of surface elements are included. The surface elements may include sensors for detecting information indicative of driving conditions, or receive information indicative of driving conditions from external devices. The surface elements may also include output elements for displaying information indicative of the driving conditions to a driver.

The configuration 305a is an example band configuration 305a of a smart ring (e.g., smart ring 101). Some of the surface elements of the housing may include interfaces 312a and 312b that may be electrically connected to, for example, the charging unit 130 or the communications unit 160. On the outside of the configuration 305a, the interfaces 312a and 312b may be electrically or optically connected with a charger to transfer energy from the charger to a battery (e.g., the battery 120), or with another device to transfer data to or from the ring 305a. The outer surface of the configuration 305a may include a display 390a, while the inner surface may include a biometric sensor 350a.

Configurations 305b and 305c are examples of configurations of a smart ring with multiple housing parts (e.g., the configuration 205b in FIG. 2). Two (or more) parts may be separate axially (the configuration 305b), azimuthally (the configuration 305c), or radially (nested rings, not shown). The parts may be connected mechanically, electrically, or optically via, for example, interfaces analogous to the interfaces 312a and 312b in configuration 305a. Each part of a smart ring housing may have one or more surface elements, such as, for example, sensors 350b and 350c or output elements 390b and 390c. The latter may be e-ink displays (e.g., output element 390b) or haptic feedback devices (e.g., output element 390c), among other suitable sensor or output devices. Additionally or alternatively, at least some of the surface elements (e.g., microphones, touch sensors) may belong to the user input unit 170.

The configuration 305d may be an example of a band and platform configuration (e.g., the configuration 205c), while the configurations 305e and 305f may be examples of the partial ring configurations 205d and 205e, respectively. Output devices 390d, 390e, and/or 390f on the corresponding configurations 305d, 305e, and/or 305f may be LCD displays, OLED displays, e-ink displays, one or more LED pixels, speakers, or any other suitable output devices that may be a part of a suite of outputs represented by an output unit (e.g., the output unit 190).

The configuration 305g is an example of a band with a one or more output devices 390g disposed on an outer surface 310g and an inner surface 311g of the ring band. In embodiments, the output devices 390g may be disposed on first and second side surfaces 308g and 309g of the ring band. Alternatively, the output devices 390g may be disposed within the inner and outer surfaces 310g and 311g, or the first and second side surfaces 308g and 309g, of the ring band configured to be viewed by a user of the smart ring configuration 305g. For example, in embodiments the outer and inner surfaces 310g and 311g or first and second side surfaces 308g and 309g may be transparent. The output devices 390g may be viewable from the entirety of the outer surface 310g, the entirety of the inner surface 311g, the entirety of the first side surface 308g, or the entirety of the second side surface 309g respectively. In embodiments, the output devices 390g may be disposed on or viewable from only a portion of each of the surfaces 310g and 311g. Additionally, sensors may be operatively coupled to the configuration 305g (e.g., elements and sensors of the user input unit 170 of FIG. 1) to detect a user input to determine where on the output devices 390g information should be displayed. For example, a user may press a finger or stylus on the outer surface 310g to indicate the information should be displayed on the outer surface 310g. Alternatively, the ring may be removed from a finger, or digit, of a user, or wearer, of the smart ring, and the user may press a finger or stylus on the inner surface 311g to indicate that information should be displayed on the inner surface 311g. The output device 390g on the inner surface 311g may then display the information for a user to view the information while the smart ring is not worn by the user of the smart ring device having the configuration 305g. A user of the configuration 305g may prefer information to be selectively viewable from the outer or inner surfaces 310g and 311g, or the first and second side surfaces 308g and 309g, depending on the type of information, potential content of the information, a current environment where the user is viewing the information, or depending on privacy concerns among other considerations. Alternatively, a user may press on a surface to indicate where the information should not be displayed.

Elements of the user input unit 170 may be coupled to the output devices 390g and a user my press on a portion of the output devices 390g to indicate that information should be presented from the portion of the output devices 390g that was pressed. Additionally, a user may indicate where the output devices 390g should display information dependent on different types of user inputs (e.g., audio input, twisting of the ring, removal of the smart ring from a finger or digit, placement of the ring on a finger or digit, a physical orientation of the ring, a change in orientation of the ring, etc.). In embodiments, the smart ring configurations 305a, 305b, 305c, 305d, 305e, 305f, and/or 305g may include an inertial motion unit (IMU) for detecting the orientation and/or the movement of the ring having one of the configurations 305a, 305b, 305c, 305d, 305e, 305f, and/or 305g. The orientation or a change in the orientation of the smart ring configuration 305a, 305b, 305c, 305d, 305e, 305f, and/or 305g may be analyzed by a processor of the smart ring configurations 305a, 305b, 305c, 305d, 305e, 305f, and/or 305g to determine which of the output devices 390a, 390b, 390c, 390d, 390e, 390f, and/or 390g to display the information, or to determine a portion, or portions, of the output devices 390a, 390b, 390c, 390d, 390e, 390f, and/or 390g that are to display information. In embodiments, the output devices 390a, 390b, 390c, 390d, 390e, 390f, and/or 390g may display an indication of a message or information that is ready to be presented to a user. The user may then provide the user input to the smart ring, based at least in part upon the indication, to indicate which output device 390g should display the information, and/or what portion of the output device should display the information. Enabling the user to indicate a portion of the display for displaying information may be useful in a number of contexts. For example, this feature enables a user to selectively view information at a time and portion (e.g., on the inside surface of the band when the band is removed) when he or she alone can view the information, thus providing the user with privacy he or she might not otherwise have. Further, in some embodiments, the band may have a display that occupies a significant portion of the outer band. In such embodiments, portions of the display may not be viewable by the user (e.g., because those portions may be viewable only from the palm-side of the hand). Thus, in such embodiments it may be advantageous to enable the user to indicate a desired portion for display (e.g., a portion of the display viewable from the back-side of the hand).

The configuration 305h may be an example of a band with a one or more output devices 390h that are multiple strips that wrap around the band. In embodiments, the output devices 390h may be a plurality of e-ink displays. The e-ink displays may display characters, symbols, messages, images, colors or other visual indications to communicate information to a user. The output devices 390h may each be coupled to individual respective e-ink displays (e.g., e-ink segmented displays, e-ink matrix displays, color e-ink displays, etc.), so that each of the output devices can present different colors, characters, symbols, or messages indicative of different information. For example, one of the output devices 305h may display a visual indication to indicate status or operations of the smart ring (e.g., battery life, downloading information, upload information, communication link status, etc.), and another of the output devices 305h may display a visual indication to convey information pertaining to biometrics of a user of the smart ring (e.g., pulse rate, blood-oxygen level, blood flow information, temperature, etc.), while yet another of the output devices 305h may be configured to change color to convey information indicative of status of a vehicle component, or vehicle operation (e.g., low fuel, temperature of an engine, tire air pressure, speed, etc.). Visual indications may include any of a character, a word, a sentence, a symbol, an image, a color, a brightness level, or another visual indication. While illustrated as three strips, the output devices 305h wrapping the band may be 1 strip, 2 strips, 4 strips, 5 strips, 6 strips, or greater, depending on the spatial dimensions of the strips and the band.

IV. Example Smart Ring E-Ink Displays

Staying with FIG. 3, the output devices 390a, 390b, 390c, 390d, 390e, 390f, 390g, and/or 390h may be e-ink displays for displaying information indicative of one or more driving conditions identified by the smart ring. The e-ink displays may be color e-ink displays, black and white e-ink displays segmented e-ink displays, matrix e-ink displays, or another type of e-ink display.

The output devices 390*a*, 390*b*, 390*c*, 390*d*, 390*e*, 390*f*, 390*g*, and/or 390*h* may change color to convey information indicative of driving conditions to a user of a smart ring. For example, the output devices 390*a*, 390*b*, 390*c*, 390*d*, 390*e*, 390*f*, 390*g*, and/or 390*h* may change to the visual indication to indicate a low battery charge level, or other malfunction, of the smart ring. Additionally, e-ink displays of the output devices 390*a*, 390*b*, 390*c*, 390*d*, 390*e*, 390*f*, 390*g*, and/or 390*h* may be configured to display any visual indication (e.g., a character, a word, a sentence, a symbol, an image, a color, a brightness level, etc.) to indicate any type of operation or status of the smart ring. For example, the output devices 390*a*, 390*b*, 390*c*, 390*d*, 390*e*, 390*f*, 390*g*, and/or 390*h* may display visual indications based at least in part upon the battery level of the smart ring, an incoming communication being received by the smart ring, an outgoing communication being sent from the smart ring, an active or inactive communicative link between the smart ring and an external device, etc.

In embodiments, the output devices 390*a*, 390*b*, 390*c*, 390*d*, 390*e*, 390*f*, 390*g*, and/or 390*h* may display visual indications representative of detected biometrics of a user of the smart ring. For example, the smart ring may detect the pulse of a user of the smart ring, and the output devices 390*a*, 390*b*, 390*c*, 390*d*, 390*e*, 390*f*, 390*g*, and/or 390*h* may present the color red if the detected pulse rate is above a maximum pulse rate threshold or below a minimum pulse rate threshold, and the output devices 390*a*, 390*b*, 390*c*, 390*d*, 390*e*, 390*f*, 390*g*, and/or 390*h* may present the color green if the detected pulse rate is between the maximum and minimum pulse rate thresholds. Alternatively or additionally, the output devices 390*a*, 390*b*, 390*c*, 390*d*, 390*e*, 390*f*, 390*g*, and/or 390*h* may display the numerical value of the detected pulse rate. E-ink displays of the output devices 390*a*, 390*b*, 390*c*, 390*d*, 390*e*, 390*f*, 390*g*, and/or 390*h* may display a visual indication of information indicative of a pulse rate, blood flow, blood oxygen level, blood pressure, skin salinity level, temperature, weariness level, a cognoscente condition of the user, an inebriation condition of the user, or any other biological and biometric information to a user of the smart ring. Additionally, the ring may display indications of a state of a user such as erratic behavior of the sure, sleepiness of the user, stress level of the user, etc.

In embodiments, the output devices 390*a*, 390*b*, 390*c*, 390*d*, 390*e*, 390*f*, 390*g*, and/or 390*h* may display a visual indication dependent on detected vehicular statuses. For example, the smart ring may communicate with sensors of a vehicle, with a communication module of the vehicle, or with another device or network to obtain current statuses of the vehicle and parts of the vehicle. For example, the output devices 390*a*, 390*b*, 390*c*, 390*d*, 390*e*, 390*f*, 390*g*, and/or 390*h* may display a low fuel graphic or image to indicate that the gas in the tank of a vehicle is below a minimum threshold. The output devices may similarly display the color red, or another color, to indicate that the heat of the engine of the vehicle is too high or a tire of the vehicle has an air pressure below a threshold. Additionally, the output devices may display a visual indication to present information to the user indicative of an oil level, needed oil change, coolant level, exhaust fume legal compliance, break pad health, low battery charge, flat tire, alternator failure, tire alignment/misalignment, transmission issue, power steering fluid level, brake fluid level, transmission fluid level, windshield wiper fluid level, etc.

In embodiments, the output devices 390*a*, 390*b*, 390*c*, 390*d*, 390*e*, 390*f*, 390*g*, and/or 390*h* may display a visual indication dependent on vehicular operations. For example, the smart ring may communicate with sensors of the vehicle, with a communication module of the vehicle, or with another device or network to obtain a current speed of the vehicle. The output devices 390*a*, 390*b*, 390*c*, 390*d*, 390*e*, 390*f*, 390*g*, and/or 390*h* may present the numerical value of the speed (e.g., 32), or a graphic or color indicating that speed of the vehicle is above a maximum speed threshold or below a minimum speed threshold, and the output devices 390*a*, 390*b*, 390*c*, 390*d*, 390*e*, 390*f*, 390*g*, and/or 390*h* may present a different graphic or color if the detected speed is between the maximum and minimum speed thresholds. In embodiments, the output devices 390*a*, 390*b*, 390*c*, 390*d*, 390*e*, 390*f*, 390*g*, and/or 390*h* may display visual indications to present to a user information indicative of a speed of a vehicle, an acceleration of a vehicle, a current altitude of the vehicle, the lane centering of the vehicle, a fuel efficiency of the vehicle, an autopilot function status of the vehicle (e.g., autopilot is activated/not-activated), an autonomous driving function of the vehicle is operational, an autonomous driving function of the vehicle is activated, air bags are activated/de-activated, a seat belt is latched/unlatched, a temperature of the environment inside of the cabin of the vehicle, etc.

In embodiments, the output devices 390*a*, 390*b*, 390*c*, 390*d*, 390*e*, 390*f*, 390*g*, and/or 390*h* may display a visual indication dependent on external factors or environmental factors in, and around, the vehicle. For example, the smart ring may communicate with sensors of the vehicle, with a communication module of the vehicle, with communication modules of other nearby vehicles, with a mobile device of the user of the smart ring, or with another device or network to obtain information and statuses of nearby vehicles. For example, it may be communicated to the smart ring that a nearby driver is driving erratically, and the smart ring may display a warning message, a graphic, or the color red to indicate that the driver should be cautious. Additionally, the output devices may display visual indications, signals, and information indicative of current or predicated weather conditions (e.g., rain, snow, extreme heat, etc.), current external environmental conditions (e.g., wet/slick roads, fog levels, a visibility level, dangerous breathing air, external temperature, etc.), current conditions inside of the cab of the vehicle (e.g., the temperature, air quality, moisture level, etc.).

In embodiments, the output devices 390*a*, 390*b*, 390*c*, 390*d*, 390*e*, 390*f*, 390*g*, and/or 390*h* may output visual indications and signals to indicate many driving conditions during operation of a vehicle such as the congestion of drivers along a road or planned trip route, the current proximity of the vehicle to external objects outside of the vehicle (e.g., other vehicles, pedestrians, trees, etc.), or other factors associated with operation of a vehicle.

The output devices 390*a*, 390*b*, 390*c*, 390*d*, 390*e*, 390*f*, 390*g*, and/or 390*h* may display visual indications to a user of a smart ring, any number of driving conditions as described above. Driving conditions may be considered to be any element or factor that may have an influence or impact on the operation of a vehicle. For example, the weariness of an operator of the vehicle may be considered to be a driving condition, as well as the visibility of a road due to a rainstorm. The driving conditions may include one or more of the examples above including, without limitation, any operation of a vehicle, status of a vehicle or part of a vehicle, biometric of a user of the smart ring, operation of the smart ring, statuses of the smart ring, external environmental factors, and external driving factors. Additionally, it is envisioned, that the user of the smart ring may be a driver of a vehicle and the biometric information may be used to determine the sleepiness of the driver, inebriation condition of the driver, or otherwise, cognoscente condition of the driver.

While described above as "displaying visual indications", the output devices 390a, 390b, 390c, 390d, 390e, 390f, 390g, and/or 390h may provide other visual signals or outputs indicative of driving conditions. For example, the output devices 390a, 390b, 390c, 390d, 390e, 390f, 390g, and/or 390h may each portray information to a user through flashes or pulses of the e-ink display, presenting images, characters, or symbols on the e-ink display, or presenting whole sentences and messages via the e-ink displays. The output devices 390a, 390b, 390c, 390d, 390e, 390f, 390g, and/or 390h, may include one or more e-ink displays for displaying characters or symbols, and scrolling of characters or symbols, as described in simultaneous reference to FIG. 3, FIG. 4A, FIG. 4B, FIG. 4C, and FIG. 5.

V. An Example Smart Ring E-Ink Display for Displaying Characters and Symbols FIG. 4A, FIG. 4B, and FIG. 4C are example illustrations of an output device 490 having an e-ink display 492 for displaying characters and symbols indicative of driving conditions identified by a smart ring device. The output device 490 may represent an example of one or more of the output devices 390a, 390b, 390c, 390d, 390e, 390f, 390g, and/or 390h shown in FIG. 3. The e-ink display 492 may display characters, symbols, words, or sentences, to a user of a smart ring device. For example, as illustrated in FIG. 4A, the e-ink display 492 may display numerals (e.g., "32") that may be indicative of a speed of a vehicle, a number of miles traversed during operation of a vehicle, the number of miles left to get to a destination of a vehicle, biometric information of a wearer of the smart ring device, or another metric or other information as described herein.

The output device 490 may cause e-ink display 492 to display a caution message that reads "Caution: Slick Roads Ahead." The message may be too long to display at one time on the output device 490 or from one point of view of the output device 490. The output device 490 may then display characters, symbols, words, and/or sentences sequentially in frames, for example displaying the word "Caution" for a few seconds, and then displaying a new frame with the words "Slick Roads Ahead." Displaying messages in frames allows for the output device 490 to display longer messages, but may not be suitable for smooth reading of entire sentences or text messages. Therefore, as illustrated in FIG. 4B and FIG. 4C, the output device 490 may cause the e-ink display 492 to display information in the form of a message in a manner that the message is scrolled across the output device 490 in the direction 498 from right to left across the output device 490. The e-ink display 492 may display and/or scroll any characters, symbols, sentences, colors, images, or messages indicative of one or more driving conditions as described above.

Additionally, the output device 490 may display (e.g., by way of scrolling) a symbol or series of symbols, such as a happy face, thumbs up, check mark, or other symbol that may be indicative of a driving condition. For example, a smart ring device may attempt to establish a communication link with a mobile device of the user of the smart ring device, or with a communications module of a vehicle being driven by the user of the smart ring device. The output device 490 may cause the e-ink display 492 to display a check mark to indicate that the communication link has been successfully established.

FIG. 5 is a flow diagram of a method for controlling the scrolling of information across an output device (e.g., including an e-ink display) on a smart ring, such as the output device 490 of FIG. 4A, FIG. 4B, and FIG. 4C. Scrolling of information and controlling the scrolling of information allow for more information to be displayed by an output device of a smart ring. Additionally, scrolling of information allows for output devices of a smart ring to display longer messages, whole sentences, and other indications of information that may not fit onto a display of an output device. In embodiments, a controller or a processor may be configured to control the scrolling of the information across the output device 490. In embodiments, a processor of the smart ring including the output device 490 may be configured to scroll the information across the output device 490 according to user inputs received at the smart ring. The user inputs may cause the processor to initiate scrolling, halt scrolling, increase the speed of the scrolling, or decrease the speed of the scrolling, among other potential scrolling commands and functionalities.

At block 502, the smart ring receives, at a user input unit such as the user input unit 170, an initial user input to initiate the scrolling of information across the output device 490. In embodiments, the user input unit 170 may include a haptic sensor, a microphone or audio sensor, an optical sensor, a pressure sensor, an accelerometer, a button, a switch, an orientation sensor that detects the physical orientation of the smart ring, or another sensor. In embodiments, the user input may include a haptic input, audio input (e.g., audio command from a user), a current physical orientation of the smart ring, a change in orientation of the smart ring, an activation of a button, an activation of a switch, a captured image (e.g., an image of a user looking at the smart ring), etc. At block 504, the smart ring initiates the scrolling of the information across the output device 490.

After initiation of the scrolling of the information, the user input unit 170 may receive a secondary user input at block 506, a tertiary user input at block 508, or a halting user input at block 510. At block 512, the processor may cause the output device 490 to increase the scrolling speed of the information across the output device 490 in response to receiving the secondary user input at block 506. Alternatively, at block 514, the processor may cause the output device 490 to decrease the scrolling speed in response to receiving the tertiary user input at block 508. Additionally, at block 516, the processor may cause the output device 490 to halt the scrolling in response to receiving the halting user input at block 510. At block 518, the processor checks to see if an end condition has been met. The end condition may include the scrolling of the entire message or information across the output device 490, a change in orientation of the smart ring device, a sensor input (e.g., imaging of a user face observing/not observing the output device 490, haptic input such as clenching of a fist, rotation of ring, a change in the orientation of the smart ring, etc.), a timing out of a display time for the information, etc. At block 520, if the terminating condition has been met, the processor may cause the output device 490 to stop presenting the information and may cause the smart ring device to resume previous displays on the output device 490, may clear the e-ink display 492 of the output device 490, or may cause the output device 490 to display other messages, images, or information. Otherwise, if the terminating condition has not been met, the current scrolling state (e.g., speeding up the scrolling, halting of the scrolling, etc.) may be applied and the information may continue to scroll, or otherwise be displayed, on the output device 490, and further user inputs may be received by the user input unit 170.

Additionally, the method 500 may include a block or step (not shown) in which a terminating user input is received by the user input unit 170 at any time during the method 500. The terminating user input may cause the processor to directly proceed to block 520, thereby ending implementation of the method 500.

Examples of each of the secondary, tertiary, and halting user inputs include: a haptic input, audio input (e.g., audio command from a user), a current physical orientation of the smart ring, a change in orientation of the smart ring, an activation of a button, an activation of a switch, a captured image (e.g., an image of a user looking at the smart ring), etc. Each of the user inputs may be dependent on a current state of the scrolling (e.g., a currently halted scrolling, a current speed of the scrolling, etc.). Additional functionalities are also envisioned such as a rewinding of the scrolling allowing a user of the smart ring device to review information that has already scrolled off of the e-ink display 492 of the output device 490.

In embodiments, the output unit 190 of FIG. 1, the output devices 390*a*, 390*b*, 390*c*, 390*d*, 390*e*, 390*f*, 390*g*, and/or 390*h*, and/or the output device 490, may include LEDs or an e-ink display, and may be configured to illuminate the LEDs or e-ink display in specific patterns, generating an optical signal, to transmit information from a smart ring to another device or system. For example, the LEDs may generate optical pulses that transmit bits of information to an optical sensor to identify a user of the smart ring. In other examples, an e-ink display of the output units 190 or 490 may display coded information such as a UPC code, QR code, 2D barcode, PDF417 code, AZTEC code, or another coded image or graphic to transmit information to an optical sensor to identify a user of the smart ring. One specific example includes communication, via an image or optical output from the output unit 190 or output devices 490*a-h*, the identification of a wearer of the smart ring to a smart lock or electronic lock of a vehicle. The optical signal received by the electronic lock may unlock the door depending on a confirmed identification of the wearer of the smart ring being an approved driver of the vehicle. Another example includes identifying the wearer of the smart ring to provide permissions to the wearer to operate a vehicle, to obtain statuses of the vehicle parts (e.g., engine performance information, coolant levels, etc.), to obtain a list or timestamped list of previous drivers of the vehicle, to obtain a history of maintenances performed on a vehicle, etc. Permissions may include providing access to an account associated with the wearer of the ring to transmit data and information from the smart ring device to a device (e.g., cellular device, network, laptop, etc.) accessing the account associated with the wearer of the smart ring, or to transmit data and information from a device accessing the account associated with the wearer of the smart ring to the smart ring device. The optical signal (e.g., captured image, optical pulse, etc.) may be used to identify a user for logging into devices and computers, determining permissions to enter a room, permissions to open a cabinet or closet, identification and permissions at a medical facility, identification and permissions at an educational institution, clocking into/out of a work place, and identification for operation of a vehicle, among other identification purposes. The output unit 190 and output devices 390*a*, 390*b*, 390*c*, 390*d*, 390*e*, 390*f*, 390*g*, and/or 390*h*, and 490 may be configured to provide the optical signal (e.g., image, graphic, optical pulse, encoded optical image or signal, etc.) to an optical fiber, optical waveguide, photodiode, avalanche photodiode, charge-coupled device, photoresistor, photomultiplier, imaging camera, or other optical sensor. Additionally, the optical signal provided by the output unit 190 may include one or more signal modulations including, but not limited to, on-off keying, amplitude shift keying, frequency shift key, binary phase shift keying, phase modulations, amplitude modulation, spatial modulations, polarization modulation, or a quadrature amplitude modulation.

It should be appreciated that a variety of suitable surface elements may be disposed at the illustrated configurations 305*a*, 305*b*, 305*c*, 305*d*, 305*e*, and/or 305*f* at largely interchangeable locations. For example, the output elements 390*d*, 390*e*, and/or 390*f* may be replaced with sensors (e.g., UV sensor, ambient light or noise sensors, etc.), user input devices (e.g., buttons, microphones, etc.), interfaces (e.g., including patch antennas or optoelectronic components communicatively connected to communications units), or other suitable surface elements.

VI. Example Devices with which a Smart Ring May Interact

FIG. 6 illustrates an example environment 400 within which a smart ring 405 including an e-ink display, such as the display 492, may be configured to operate. Elements of the environment 400 may obtain information indicative of driving conditions, communicate them to the smart ring 405, and the smart ring 405 may display information indicative of the driving conditions via output elements of the smart ring (e.g., an e-ink display). In an embodiment, the smart ring 405 may be the smart ring 101. In some embodiments, the smart ring 405 may be any suitable smart ring capable of providing at least some of the functionality described herein. Depending on the embodiment, the smart ring 405 may be configured in a manner similar or equivalent to any of the configurations 205*a*, 205*b*, 205*c*, 205*d*, 205*e*, and/or 205*f* or 305*a*, 305*b*, 305*c*, 305*d*, 305*e*, and/or 305*f* shown in FIG. 2 and FIG. 3.

The smart ring 405 may interact (e.g., by sensing, sending data, receiving data, receiving energy) with a variety of devices, such as bracelet 420 or another suitable wearable device, a mobile device 422 (e.g., a smart phone, a tablet, etc.) that may be, for example, the user device 104, another ring 424 (e.g., another smart ring, a charger for the smart ring 405, etc.), a secure access panel 432, a golf club 434 (or another recreational accessory), a smart ring 436 worn by another user, or a steering wheel 438 (or another vehicle interface). Additionally or alternatively, the smart ring 405 may be communicatively connected to a network 440 (e.g., WiFi, 5G cellular), and by way of the network 440 (e.g., network 105 in FIG. 1) to a server 442 (e.g., server 107 in FIG. 1) or a personal computer 444 (e.g., mobile device 106). Additionally or alternatively, the ring 405 may be configured to sense or harvest energy from natural environment, such as the sun 450.

The ring 405 may exchange data with other devices by communicatively connecting to the other devices using, for example, the communication unit 160. The communicative connection to other device may be initiated by the ring 405 in response to user input via the user input unit 170, in response to detecting trigger conditions using the sensor unit 150, or may be initiated by the other devices. The communicative connection may be wireless, wired electrical connection, or optical. In some implementation, establishing a communicative link may include establishing a mechanical connection. The ring 405 may display or otherwise convey to a user of the ring 405 information or data received from any devices communicatively coupled to the ring 405, and more specifically data indicative of one or more driving conditions as described herein.

The ring 405 may connect to other devices (e.g., a device with the charger 103 built in) to charge the battery 120. The connection to other devices for charging may enable the ring 405 to be recharged without the need for removing the ring 405 from the finger. For example, the bracelet 420 may include an energy source that may transfer the energy from the energy source to battery 120 of the ring 405 via the charging unit 430. To that end, an electrical (or optical) cable may extend from the bracelet 420 to an interface (e.g., interfaces 112a, 112b, 312a and 312b) disposed at the housing (e.g., housings 110, 210a, 210b, 210c, 210d, 210e, 210f, 210g, 210h, and/or 210i) of the ring 405. The mobile device 422, the ring 424, the golf club 434, the steering wheel 438 may also include energy source configured as chargers (e.g., the charger 103) for the ring 405. The chargers for may transfer energy to the ring 405 via a wired or wireless (e.g., inductive coupling) connection with the charging unit 130 of the ring 405.

VI. Examples of Other Considerations

When implemented in software, any of the applications, services, and engines described herein may be stored in any tangible, non-transitory computer readable memory such as on a magnetic disk, a laser disk, solid state memory device, molecular memory storage device, or other storage medium, in a RAM or ROM of a computer or processor, etc. Although the example systems disclosed herein are disclosed as including, among other components, software or firmware executed on hardware, it should be noted that such systems are merely illustrative and should not be considered as limiting. For example, it is contemplated that any or all of these hardware, software, and firmware components could be embodied exclusively in hardware, exclusively in software, or in any combination of hardware and software. Accordingly, while the example systems described herein are described as being implemented in software executed on a processor of one or more computer devices, persons of ordinary skill in the art will readily appreciate that the examples provided are not the only way to implement such systems.

The described functions may be implemented, in whole or in part, by the devices, circuits, or routines of the system 100 shown in FIG. 1. Each of the described methods may be embodied by a set of circuits that are permanently or semi-permanently configured (e.g., an ASIC or FPGA) to perform logical functions of the respective method or that are at least temporarily configured (e.g., one or more processors and a set instructions or routines, representing the logical functions, saved to a memory) to perform the logical functions of the respective method.

While the present disclosure has been described with reference to specific examples, which are intended to be illustrative only and not to be limiting of the present disclosure, it will be apparent to those of ordinary skill in the art that changes, additions or deletions may be made to the disclosed embodiments without departing from the spirit and scope of the present disclosure.

Throughout this specification, plural instances may implement components, operations, or structures described as a single instance. Although individual operations of one or more methods are illustrated and described as separate operations, one or more of the individual operations may be performed concurrently in certain embodiments.

As used herein, any reference to "one embodiment" or "an embodiment" means that a particular element, feature, structure, or characteristic described in connection with the embodiment is included in at least one embodiment. The appearances of the phrase "in one embodiment" in various places in the specification may not be all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements may not be limited to only those elements but may include other elements not expressly listed or inherent to such process, method, article, or apparatus. Further, unless expressly stated to the contrary, "or" refers to an inclusive "or" and not to an exclusive "or." For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. Generally speaking, when a system or technique is described as including "a" part or "a" step, the system or technique should be read to include one or at least one part or step. Said another way, for example, a system described as including a blue widget may include multiple blue widgets in some implementations (unless the description makes clear that the system includes only one blue widget).

X. General Terms and Phrases

Throughout this specification, some of the following terms and phrases are used.

Bus according to some embodiments: Generally speaking, a bus is a communication system that transfers information between components inside a computer system, or between computer systems. A processor or a particular system (e.g., the processor 454 of the server 442) or subsystem may communicate with other components of the system or subsystem (e.g., the components 452 and 456) via one or more communication links. When communicating with components in a shared housing, for example, the processor may be communicatively connected to components by a system bus. Unless stated otherwise, as used herein the phrase "system bus" and the term "bus" refer to: a data bus (for carrying data), an address bus (for determining where the data should be sent), a control bus (for determining the operation to execute), or some combination thereof. Depending on the context, "system bus" or "bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Communication Interface according to some embodiments: Some of the described devices or systems include a "communication interface" (sometimes referred to as a "network interface"). A communication interface enables the system to send information to other systems and to receive information from other systems, and may include circuitry for wired or wireless communication.

Each described communication interface or communications unit (e.g., communications unit 160) may enable the device of which it is a part to connect to components or to other computing systems or servers via any suitable network, such as a personal area network (PAN), a local area network (LAN), or a wide area network (WAN). In particular, the communication unit 160 may include circuitry for wirelessly connecting the smart ring 101 to the user device 104 or the network 105 in accordance with protocols and standards for NFC (operating in the 13.56 MHz band), RFID (operating in frequency bands of 125-134 kHz, 13.56 MHz, or 856 MHz to 960 MHz), Bluetooth (operating in a band of 2.4 to 2.485 GHz), Wi-Fi Direct (operating in a band of 2.4 GHz or 5 GHz), or any other suitable communications protocol or standard that enables wireless communication.

Communication Link according to some embodiments: A "communication link" or "link" is a pathway or medium connecting two or more nodes. A link between two end-nodes may include one or more sublinks coupled together via one or more intermediary nodes. A link may be a physical link or a logical link. A physical link is the interface or medium(s) over which information is transferred, and may be wired or wireless in nature. Examples of physicals links may include a cable with a conductor for transmission of electrical energy, a fiber optic connection for transmission of light, or a wireless electromagnetic signal that carries information via changes made to one or more properties of an electromagnetic wave(s).

A logical link between two or more nodes represents an abstraction of the underlying physical links or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as a "communication channel." In a wireless communication system, the term "communication channel" (or just "channel") generally refers to a particular frequency or frequency band. A carrier signal (or carrier wave) may be transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

Memory and Computer-Readable Media according to some embodiments: Generally speaking, as used herein the phrase "memory" or "memory device" refers to a system or device (e.g., the memory unit 144) including computer-readable media ("CRM"). "CRM" refers to a medium or media accessible by the relevant computing system for placing, keeping, or retrieving information (e.g., data, computer-readable instructions, program modules, applications, routines, etc.). Note, "CRM" refers to media that is non-transitory in nature, and does not refer to disembodied transitory signals, such as radio waves.

The CRM may be implemented in any technology, device, or group of devices included in the relevant computing system or in communication with the relevant computing system. The CRM may include volatile or nonvolatile media, and removable or non-removable media. The CRM may include, but is not limited to, RAM, ROM, EEPROM, flash memory, or other memory technology, CD-ROM, digital versatile disks (DVD) or other optical disk storage, magnetic cassettes, magnetic tape, magnetic disk storage or other magnetic storage devices, or any other medium which can be used to store information, and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is circuitry that manages the flow of data between the CRM and the system bus.

Network according to some embodiments: As used herein and unless otherwise specified, when used in the context of system(s) or device(s) that communicate information or data, the term "network" (e.g., the networks 105 and 440) refers to a collection of nodes (e.g., devices or systems capable of sending, receiving or forwarding information) and links which are connected to enable telecommunication between the nodes.

Each of the described networks may include dedicated routers responsible for directing traffic between nodes, and, optionally, dedicated devices responsible for configuring and managing the network. Some or all of the nodes may be also adapted to function as routers in order to direct traffic sent between other network devices. Network devices may be inter-connected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. If desired, each described network may include networks or sub-networks, such as a local area network (LAN) or a wide area network (WAN).

Node according to some embodiments: Generally speaking, the term "node" refers to a connection point, redistribution point, or a communication endpoint. A node may be any device or system (e.g., a computer system) capable of sending, receiving or forwarding information. For example, end-devices or end-systems that originate or ultimately receive a message are nodes. Intermediary devices that receive and forward the message (e.g., between two end-devices) are also generally considered to be "nodes."

Processor according to some embodiments: The various operations of example methods described herein may be performed, at least partially, by one or more processors (e.g., the one or more processors in the processor unit 142). Generally speaking, the terms "processor" and "microprocessor" are used interchangeably, each referring to a computer processor configured to fetch and execute instructions stored to memory. By executing these instructions, the processor(s) can carry out various operations or functions defined by the instructions. The processor(s) may be temporarily configured (e.g., by instructions or software) or permanently configured to perform the relevant operations or functions (e.g., a processor for an Application Specific Integrated Circuit, or ASIC), depending on the particular embodiment. A processor may be part of a chipset, which may also include, for example, a memory controller or an I/O controller. A chipset is a collection of electronic components in an integrated circuit that is typically configured to provide I/O and memory management functions as well as a plurality of general purpose or special purpose registers, timers, etc. Generally speaking, one or more of the described processors may be communicatively coupled to other components (such as memory devices and I/O devices) via a system bus.

The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Although specific embodiments of the present disclosure have been described, it will be understood by those of skill in the art that there are other embodiments that are equivalent to the described embodiments. Accordingly, it is to be understood that the present disclosure is not to be limited by the specific illustrated embodiments.

What is claimed is:

1. A system for displaying information indicative of driving conditions to a driver via a smart ring device comprising:
    a ring band having a plurality of surfaces including an inner surface, an outer surface, a first side surface and a second side surface;
    a processor disposed within the ring band and configured to:
        receive data from:
            a communication module disposed within the ring band, or
            from one or more sensors disposed within the ring band; and
        analyze the data to identify one or more driving conditions, the one or more driving conditions including at least one selected from a group consisting of a vehicular status and a vehicular operation; and
    an electronic ink (e-ink) display disposed on at least one of the plurality of surfaces of the ring band and communicatively coupled to the processor, wherein the processor is configured to cause the e-ink display to present information indicative of the identified one or more driving conditions.

2. A system according to claim 1, wherein the e-ink display comprises an e-ink display disposed on one or more of: the first side surface of the ring band or the second side surface of the ring band.

3. A system according to claim 1, further comprising a user input unit communicatively coupled to the processor; wherein the processor is further configured to cause the e-ink display to present the information indicative of the identified one or more driving conditions within a selected portion of the e-ink display in response to receiving, via the user input unit, a user input representing a selection of the selected portion.

4. A system according to claim 3, wherein the user input unit comprises a touch sensor.

5. A system according to claim 3, wherein the user input unit comprises a microphone.

6. A system according to claim 1, wherein the processor is further configured to cause the e-ink display to present the information indicative of the identified one or more driving conditions by scrolling the information indicative of the identified one or more driving conditions across the e-ink display.

7. A system according to claim 6, further comprising a user input unit communicatively coupled to the processor, and wherein the processor is further configured to:
    initiate the scrolling of the information indicative of the identified one or more driving conditions upon receiving, via the user input unit, a user input;
    halt the scrolling of the information upon receiving, via the user input unit, a user input;
    increase a scrolling speed of the information upon receiving, via the user input unit, a user input; and
    decrease the scrolling speed of the information upon receiving, via the user input unit, a user input.

8. A system according to claim 1, wherein the information indicative of the identified one or more driving conditions includes one of a speed of a vehicle, an acceleration of a vehicle, a current weather condition, a sleepiness condition of a driver, a cognoscente condition of a driver, an operational status of a vehicle, an inebriation condition of a driver, and biometric information of a wearer of the smart ring device.

9. A system according to claim 1, wherein the one or more sensors comprises a biometric sensor configured to monitor biometric information for a wearer of the smart ring and further configured to transmit, via the communication module, the biometric information to a mobile device associated with the driver of the vehicle.

10. A system according to claim 1, wherein the processor is configured to receive, via the communication module, the data from a mobile device associated with a driver of the vehicle, and wherein the mobile device is configured to obtain the data from sensors of the vehicle.

11. A method of displaying information indicative of driving conditions to a driver via a smart ring device comprising:
    receiving, by a processor disposed in a ring band of a smart ring device configured to be worn by a driver of a vehicle, data from:
        a communication module disposed within the ring band, or
        one or more sensors disposed within the ring band;
    analyzing, by the processor, the data to identify one or more driving conditions, the one or more driving conditions including at least one selected from a group consisting of a vehicular status and a vehicular operation; and
    displaying information indicative of the identified one or more driving conditions via an electronic ink (e-ink) display disposed on at least one of a plurality of surfaces of the ring band, wherein the plurality of surfaces includes an inner surface, an outer surface, a first side surface, and a second side surface.

12. A method according to claim 11, wherein the e-ink display comprises an e-ink display disposed on one or more of: the first side surface of the ring band or the second side surface of the ring band.

13. A method according to claim 11, wherein displaying the information indicative of the identified one or more driving conditions comprises:
displaying the information within a selected portion of the e-ink display in response to receiving a user input representing a selection of the selected portion.

14. A method according to claim 13, wherein the user input comprises a haptic input.

15. A method according to claim 13, wherein the user input comprises a user input via a microphone.

16. A method according to claim 11, wherein displaying the information indicative of the identified one or more driving conditions comprises:
causing, by the processor, the e-ink display to present the information indicative of the identified one or more driving conditions by scrolling the information indicative of the identified one or more driving conditions across the e-ink display.

17. A method according to claim 16, further comprising:
initiating, by the processor, the scrolling of the information indicative of the identified one or more driving conditions upon receiving, via a user input unit, a user input;
halting, by the processor, a scrolling of the information upon receiving, via the user input unit, a user input;
increasing, by the processor, a scrolling speed of the information upon receiving, via the user input unit, a user input; and
decreasing, by the processor, the scrolling speed of the information upon receiving, via the user input unit, a user input.

18. A method according to claim 11, wherein the information indicative of the identified one or more driving conditions includes one of a speed of a vehicle, an acceleration of a vehicle, a current weather condition, a sleepiness condition of a driver, a cognoscente condition of a driver, an operational status of a vehicle, an inebriation condition of a driver, and biometric information of a wearer of the smart ring device.

19. A method according to claim 11, wherein receiving the data comprises receiving the data, via the communication module, from a mobile device that is associated with a driver of a vehicle, and wherein the mobile device is configured to obtain the data from one or more sensors of the vehicle.

20. A method according to claim 11, wherein the one or more sensors disposed within the ring band comprises a biometric sensor and wherein the method further comprises:
monitoring, by the biometric sensor, biometric information of the driver of the vehicle; and
transmitting, via the communication module, the biometric information to a mobile device associated with the driver of the vehicle.

* * * * *